(12) United States Patent
Evans et al.

(10) Patent No.: US 9,150,574 B2
(45) Date of Patent: Oct. 6, 2015

(54) ENZYME INHIBITOR COMPOUNDS

(75) Inventors: David Evans, London (GB); Allison Carley, London (GB); Alison Stewart, London (GB); Michael Higginbottom, London (GB); Edward Savory, London (GB); Iain Simpson, London (GB); Marianne Nilsson, Stockholm (SE); Martin Haraldsson, Stockholm (SE); Erik Nordling, Stockholm (SE); Tobias Koolmeister, Stockholm (SE)

(73) Assignee: Proximagen Limited, London (GB)

( * ) Notice: Subject to any disclaimer, the term of this patent is extended or adjusted under 35 U.S.C. 154(b) by 0 days.

(21) Appl. No.: 14/344,417

(22) PCT Filed: Sep. 14, 2011

(86) PCT No.: PCT/EP2011/065967
§ 371 (c)(1),
(2), (4) Date: Jul. 3, 2014

(87) PCT Pub. No.: WO2013/037411
PCT Pub. Date: Mar. 21, 2013

(65) Prior Publication Data
US 2014/0357623 A1  Dec. 4, 2014

(51) Int. Cl.
C07D 471/02 (2006.01)
A61K 31/55 (2006.01)
C07D 471/04 (2006.01)

(52) U.S. Cl.
CPC .................................... *C07D 471/04* (2013.01)

(58) Field of Classification Search
None
See application file for complete search history.

(56) References Cited

U.S. PATENT DOCUMENTS

2007/0254867 A1  11/2007  Hasvold et al.
2013/0102587 A1*  4/2013  Evans et al. ............... 514/211.15

FOREIGN PATENT DOCUMENTS

| | | |
|---|---|---|
| DE | 19649460 A1 | 5/1998 |
| WO | 96-40686 A1 | 12/1996 |
| WO | 01-19821 A1 | 3/2001 |
| WO | 02-38153 A1 | 5/2002 |
| WO | 03-006003 A1 | 1/2003 |
| WO | 03-029209 A2 | 4/2003 |
| WO | 2005-014530 A2 | 2/2005 |
| WO | 2005-040169 A2 | 5/2005 |
| WO | 2005-074603 A2 | 8/2005 |
| WO | 2005116028 A2 | 12/2005 |
| WO | 2006-114180 A1 | 11/2006 |
| WO | 2007-002667 A2 | 1/2007 |
| WO | 2007-120528 A2 | 10/2007 |
| WO | 2007115315 A2 | 10/2007 |
| WO | 2007-134828 A1 | 11/2007 |
| WO | 2008-088744 A1 | 7/2008 |
| WO | 2008-135442 A1 | 11/2008 |
| WO | 2009-080682 A1 | 7/2009 |
| WO | 2009-095162 A1 | 8/2009 |
| WO | 2009-108551 A2 | 9/2009 |
| WO | 2010-031789 A1 | 3/2010 |

(Continued)

OTHER PUBLICATIONS

International Search Report dated Oct. 21, 2011, for PCT/EP2011/065967, filed on Sep. 14, 2011.

(Continued)

*Primary Examiner* — Heidi Reese
(74) *Attorney, Agent, or Firm* — Sean B. Mahoney

(57) ABSTRACT

2-{4-[1-(4-chlorophenyl)-1H-pyrrolo[2,3-c]pyridin-3-yl]piperidin-1-yl}ethan-1-amine; 3-aminopropyl 4-[1-(4-chlorophenyl)-1H-pyrrolo[2,3-c]pyridin-3-yl]piperidine-1-carboxylate; 1-{4-[1-(4-chlorophenyl)-1H-pyrrolo[2,3-c]pyridin-3-yl]piperidin-1-yl}-4-(dimethylamino)butan-1-one; 5-amino-1-{4-[1-(4-chlorophenyl)-1H-pyrrolo[2,3-c]pyridin-3-yl]piperidin-1-yl}pentan-1-one; N-(2-aminoethyl)-4-[1-(4-chlorophenyl)-1H-pyrrolo[2,3-c]pyridin-3-yl]piperidine-1-carboxamide; N-(3-aminopropyl)-4-[1-(4-chlorophenyl)-1H-pyrrolo[2,3-c]pyridin-3-yl]piperidine-1-carboxamide; 4-[1-(4-chlorophenyl)-1H-pyrrolo[2,3-c]pyridin-3-yl]-N-[3-(dimethylamino)propyl]piperidine-1-carboxamide; 1-({4-[1-(4-chlorophenyl)-1H-pyrrolo[2,3-c]pyridin-3-yl]piperidin-1-yl}carbonyl)piperazine; 4-({4-[1-(4-chlorophenyl)-1H-pyrrolo[2,3-c]pyridin-3-yl]piperidin-1-yl}carbonyl)morpholine; 1-({4-[1-(4-chlorophenyl)-1H-pyrrolo[2,3-c]pyridin-3-yl]piperidin-1-yl}carbonyl)-1,4-diazepane; ethyl 1-[1-(4-chlorophenyl)-1H-pyrazolo[3,4-c]pyridin-3-yl]piperidine-4-carboxylate; ethyl 1-[1-(4-methylphenyl)-1H-pyrazolo[3,4-c]pyridin-3-yl]piperidine-4-carboxylate; 1-[1-(4-chlorophenyl)-1H-pyrazolo[3,4-c]pyridin-3-yl]piperidine-4-carboxylic acid; N-(2-aminoethyl)-1-[1-(4-chlorophenyl)-1H-pyrazolo[3,4-c]pyridin-3-yl]piperidine-4-carboxamide; 4-({1-[1-(4-chlorophenyl)-1H-pyrazolo[3,4-c]pyridin-3-yl]piperidin-4yl}carbonyl)morpholine; 1-({1-[1-(4-chlorophenyl)-1H-pyrazolo[3,4-c]pyridin-3-yl]piperidin-4-yl}carbonyl)piperazine; {4-[1-(4-methylphenyl)-1H-pyrazolo[3,4-c]pyridin-3-yl]morpholin-3-yl}methanol; {4-[1-(4-methylphenyl)-1H-pyrazolo[3,4-c]pyridin-3-yl]morpholin-2-yl}methanol; [(3R)-4-[1-(4-chlorophenyl)-1H-pyrazolo[3,4-c]pyridin-3-yl]morpholin-3-yl]methanol; methyl 4-[1-(4-chlorophenyl)-1H-pyrazolo[3,4-c]pyridin-3-yl]morpholine-3-carboxylate; N-(2-aminoethyl)-4-[1-(4-chlorophenyl)-1H-pyrazolo[3,4-c]pyridin-3-yl]morpholine-3-carboxamide; 2-{4-[1-(4-chlorophenyl)-1H-pyrazolo[3,4-c]pyridin-3-yl]morpholin-3-yl}ethan-1-ol; methyl 1-[1-(4-chlorophenyl)-1H-pyrazolo[3,4-c]pyridin-3-yl]piperidine-2-carboxylate; N-(2-aminoethyl)-1-[1-(4-chlorophenyl)-1H-pyrazolo[3,4-c]pyridin-3-yl]piperidine-2-carboxamide; 1-({1-[1-(4-chlorophenyl)-1H-pyrazolo[3,4-c]pyridin-3-yl]piperidin-2-yl}carbonyl)piperazine; 4-[1-(4-methylphenyl)-1H-pyrrolo[2,3-c]pyridin-3-yl]morpholine; 1-(4-chlorophenyl)-3-(piperidin-4-yl)-1H-pyrrolo[2,3-c]pyridin-4-ol; N-butyl-1-(4-chlorophenyl)-N-methyl-1H-pyrazolo[3,4-c]pyridin-3-amine; 1-[4-(fluoromethyl)phenyl]-3-(oxan-4-yl)-1H-pyrazolo[3,4-c]pyridine; and 3-({4-[1-(4-chlorophenyl)-1H-pyrazolo[3,4-c]pyridin-3-yl]piperidin-1-yl}methyl)pyridine are useful for the inhibition of SSAO activity.

12 Claims, No Drawings

(56) References Cited

FOREIGN PATENT DOCUMENTS

| WO | 2010-031791 | A1 | 3/2010 |
|---|---|---|---|
| WO | 2010-064020 | A1 | 6/2010 |
| WO | 2011-019060 | A1 | 2/2011 |
| WO | 2011-113798 | A2 | 9/2011 |
| WO | 2011-113798 | A3 | 9/2011 |
| WO | 2013-038189 | A1 | 3/2013 |

OTHER PUBLICATIONS

Jordan, V.C. "Tamoxifen: A Most Unlikely Pioneering Medicine," Nature Reviews: Drug Discovery, vol. 2, Mar. 2003, pp. 205-213.

Dorwald, F. Zaragoza. Side Reactions in Organic Synthesis: A Guide to Successful Synthesis Design, Weinheim: Wiley-VCH Verlag GmbH & Co. KGaA, 2005, Preface.

Search Report dated Oct. 17, 2014 from Singapore Application No. 2012206602-3.

Boomsma et al. "Semicarbazide-sensitive amine oxidase (SSAO): from cell to circulation," Med. Sci. Monit., 2005; 11(4): RA122-126.

Dunkel, Petra et al. "Semicarbazide-sensitive amine oxidase/vascular adhesion protein-1: a patent survey," Expert Opin. Ther. Patents, 21(9): 1453-1471 (2011).

* cited by examiner

ENZYME INHIBITOR COMPOUNDS

This application is a national stage application under 35 U.S.C. §371 of PCT Patent Application No. PCT/EP2011/065967, filed Sep. 14, 2011, published as WO2013/037411, which is incorporated herein by reference in its entirety. Also incorporated by reference herein in their entirety are PCT Patent Application No. PCT/GB2012/052265, filed Sep. 13, 2012, published as WO2013/038189, and Great Britain Patent Application No. 1115853.2 filed Sep. 14, 2011.

FIELD OF THE INVENTION

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumour growth.

BACKGROUND ART

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein. Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

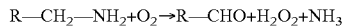

$$R\text{—}CH_2\text{—}NH_2+O_2 \rightarrow R\text{—}CHO+H_2O_2+NH_3$$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Matyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61(Pt 11), 1550-1562]. SSAO activity has been found in a variety of tissues including vascular and non-vascular smooth muscle tissue, endothelium, and adipose tissue [Lewinsohn, Braz. *J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijarvi et al., *J. Immunol.* 1998, 161, 1549-1557]. It has recently been shown that circulating human and rodent SSAO originates from the tissue-bound form [Gökürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Goktark et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, Braz. *J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijarvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mntyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., Eur. J. Immunol. 2005, 35(11), 3119-3130; Salter-Cid et al., J. Pharmacol. Exp. Ther. 2005, 315(2), 553-562; McDonald et al., Annual Reports in Medicinal Chemistry 2007, 42, 229-243; Salmi & Jalkanen, in "Adhesion Molecules: Functions and Inhibition" K. Ley (Ed.), 2007, pp. 237-251; Noda et al., FASEB J. 2008 22(4), 1094-1103; Noda et al., FASEB J. 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases. SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88; Irjala H, Salmi M, Alanen K, Gre'nman R, Jalkanen S (2001), Immunol. 166, 6937-6943; Forster-Horvath C, Dome B, Paku S, et al. (2004), Melanoma Res. 14, 135-40.). One report (Marttila-Ichihara F, Castermans K, Auvinen K, Oude Egbrink M G, Jalkanen S, Griffioen A W, Salmi M. (2010), J Immunol. 184, 3164-3173.) has shown that mice bearing enzymatically inactive VAP-1 grow melanomas more slowly, and have reduced tumour blood vessel number and diameter. The reduced growth of ic) these tumours was also reflected in the reduced (by 60-70%) infiltration of myeloid suppressor cells. Encouragingly VAP-1 deficiency had no effect on vessel or lymph formation in normal tissue.

Small molecules of different structural classes have previously been disclosed as SSAO inhibitors, for example in WO 02/38153 (tetrahydroimidazo[4,5-c]pyridine derivatives), in WO 03/006003 (2-indanylhydrazine derivatives), in WO 2005/014530 (allylhydrazine and hydroxylamine (aminooxy) compounds) and in WO 2007/120528 (allylamino compounds). Additional SSAO inhibitors are disclosed in PCT/EP2009/062011 and PCT/EP2009/062018.

Our co-pending International Patent Application No.: PCT/EP2011/053818 relates to SSAO inhibitors of formula (I) or a pharmaceutically acceptable salt, or N-oxide thereof:

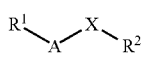

wherein
$R^1$ is phenyl or 6-membered heteroaryl, optionally substituted with one or more substituents selected from halogen, cyano, $C_{1-4}$-alkyl, halo-$C_{1-4}$-alkyl, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, and —$NR^6S(O)_2R^5$;
A is a bond;
$R^2$ is —B-Q-[$R^3$]$_n$ or —B—$R^3$;
wherein n=1, 2, 3, or 4

B is a bond, O, $NR^4$, —C(O)— or $C_{1-3}$-alkylene;
Q is saturated or partially unsaturated monocyclic 3-7 membered heterocyclic or $C_{3-7}$-cycloalkyl ring;
when $R^2$ is —B-Q-[$R^3$]$_n$, $R^3$ is selected from hydrogen, halogen, cyano, amino, hydroxyl, oxo, $C_{1-4}$-alkyl, halo-$C_{1-4}$-alkyl, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$NR^6S(O)_2R^5$, —$S(O)_2R^5$, phenyl-$C_{1-4}$-alkyl and heteroaryl-$C_{1-4}$-alkyl, and wherein any phenyl or heteroaryl residue is optionally substituted with one or more substituents selected from halogen, cyano, $C_{1-4}$-alkyl, halo-$C_{1-4}$-alkyl, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$NR^6S(O)_2R^5$;
when $R^2$ is —B—$R^3$, $R^3$ is selected from amino, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$NR^6S(O)_2R^5$, phenyl-$C_{1-4}$-alkyl and heteroaryl-$C_{1-4}$-alkyl, and wherein any phenyl or heteroaryl residue is optionally substituted with one or more substituents selected from halogen, cyano, $C_{1-4}$-alkyl, halo-$C_{1-4}$-alkyl, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$NR^6S(O)_2R^5$, provided that when $R^2$ is —B—$R^3$, and B is a bond and $R^3$ is —$C(O)R^5$, then $R^5$ is not hydrogen;
$R^{4A}$, $R^{4B}$ and $R^5$ are each independently selected from hydrogen, $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)-amino-$C_{1-4}$-alkyl or $C_{1-4}$alkoxy-$C_{1-4}$alkyl; or $R^{4A}$ and $R^{4B}$ together with the nitrogen to which they are attached form a cyclic amino group such as a piperidinyl, piperazinyl, N-substituted piperazinyl, morpholinyl or homopiperidinyl group;
$R^{4A1}$ is selected from $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl or $C_{1-4}$alkoxy-$C_{1-4}$alkyl; or $R^{4A1}$ and $R^{4B}$ together with the nitrogen to which they are attached form a cyclic amino group such as a piperidinyl, piperazinyl, N-substituted piperazinyl, morpholinyl or homopiperidinyl group;
$R^6$ is hydrogen or $C_{1-4}$-alkyl; and
X is selected from the radicals of formulae (1-16) wherein the bond marked * is attached to $R^1$A- and the bond marked ** is attached to —$R^2$:

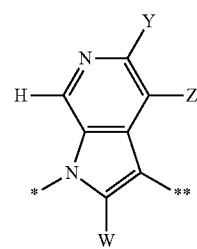

2
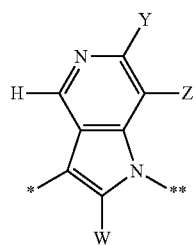
3
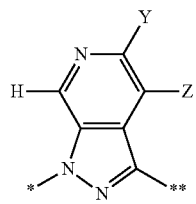
4
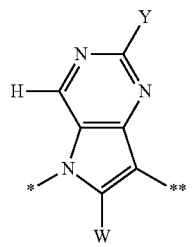
5
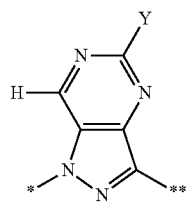
6
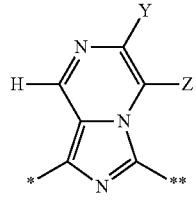
7
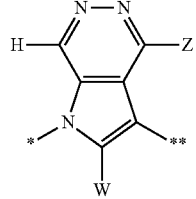
8
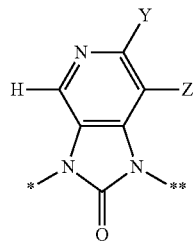
9
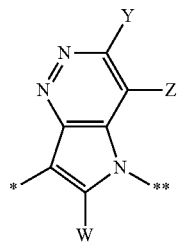
10
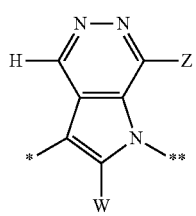
11
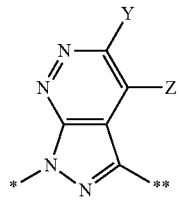
12
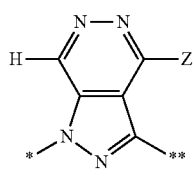
13
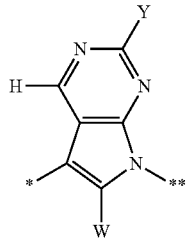
14
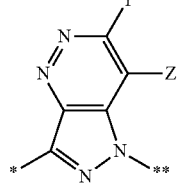
15
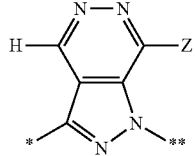

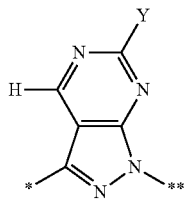

wherein Y is selected from hydrogen, hydroxyl, amino, —NHR⁶, —OCH₃;
Z is selected from hydrogen, fluorine, hydroxyl, $C_{1-4}$-alkoxy, halo-$C_{1-4}$-alkyl, CONH₂, cyano, SO₂NH₂, amino, —NHR⁶;
W is selected from H, $C_{1-4}$-alkyl, halo-$C_{1-4}$-alkyl;

BRIEF DESCRIPTION OF THE INVENTION

The present invention relates to a group of specific compounds falling within the general disclosure of PCT/EP2011/053818, but not specifically exemplified therein. The present compounds have the utilities disclosed herein.

DETAILED DESCRIPTION OF THE INVENTION

According to the invention there is provided a compound selected from the group consisting of:
2-{4-[1-(4-chlorophenyl)-1H-pyrrolo[2,3-c]pyridin-3-yl]piperidin-1-yl}ethan-1-amine;
3-aminopropyl 4-[1-(4-chlorophenyl)-1H-pyrrolo[2,3-c]pyridin-3-yl]piperidine-1-carboxylate;
1-{4-[1-(4-chlorophenyl)-1H-pyrrolo[2,3-c]pyridin-3-yl]piperidin-1-yl}-4-(dimethylamino)butan-1-one;
5-amino-1-{4-[1-(4-chlorophenyl)-1H-pyrrolo[2,3-c]pyridin-3-yl]piperidin-1-yl}pentan-1-one;
N-(2-aminoethyl)-4-[1-(4-chlorophenyl)-1H-pyrrolo[2,3-c]pyridin-3-yl]piperidine-1-carboxamide;
N-(3-aminopropyl)-4-[1-(4-chlorophenyl)-1H-pyrrolo[2,3-c]pyridin-3-yl]piperidine-1-carboxamide;
4-[1-(4-chlorophenyl)-1H-pyrrolo[2,3-c]pyridin-3-yl]-N-[3-(dimethylamino)propyl]piperidine-1-carboxamide;
1-({4-[1-(4-chlorophenyl)-1H-pyrrolo[2,3-c]pyridin-3-yl]piperidin-1-yl}carbonyl)piperazine;
4-({4-[1-(4-chlorophenyl)-1H-pyrrolo[2,3-c]pyridin-3-yl]piperidin-1-yl}carbonyl)morpholine;
1-({4-[1-(4-chlorophenyl)-1H-pyrrolo[2,3-c]pyridin-3-yl]piperidin-1-yl}carbonyl)-1,4-diazepane;
ethyl 1-[1-(4-chlorophenyl)-1H-pyrazolo[3,4-c]pyridin-3-yl]piperidine-4-carboxylate;
ethyl 1-[1-(4-methylphenyl)-1H-pyrazolo[3,4-c]pyridin-3-yl]piperidine-4-carboxylate;
1-[1-(4-chlorophenyl)-1H-pyrazolo[3,4-c]pyridin-3-yl]piperidine-4-carboxylic acid;
N-(2-aminoethyl)-1-[1-(4-chlorophenyl)-1H-pyrazolo[3,4-c]pyridin-3-yl]piperidine-4-carboxamide;
4-({1-[1-(4-chlorophenyl)-1H-pyrazolo[3,4-c]pyridin-3-yl]piperidin-4-yl}carbonyl)morpholine;
1-({1-[1-(4-chlorophenyl)-1H-pyrazolo[3,4-c]pyridin-3-yl]piperidin-4-yl}carbonyl)piperazine;
{4-[1-(4-methylphenyl)-1H-pyrazolo[3,4-c]pyridin-3-yl]morpholin-3-yl}methanol;
{4-[1-(4-methylphenyl)-1H-pyrazolo[3,4-c]pyridin-3-yl]morpholin-2-yl}methanol;
[(3R)-4-[1-(4-chlorophenyl)-1H-pyrazolo[3,4-c]pyridin-3-yl]morpholin-3-yl]methanol;
methyl 4-[1-(4-chlorophenyl)-1H-pyrazolo[3,4-c]pyridin-3-yl]morpholine-3-carboxylate;
N-(2-aminoethyl)-4-[1(4-chlorophenyl)-1H-pyrazolo[3,4-c]pyridin-3-yl]morpholine-3-carboxamide;
2-{4-[1-(4-chlorophenyl)-1H-pyrazolo[3,4-c]pyridin-3-yl]morpholin-3-yl}ethan-1-ol;
methyl 1-[1-(4-chlorophenyl)-1H-pyrazolo[3,4-c]pyridin-3-yl]piperidine-2-carboxylate;
N-(2-aminoethyl)-1-[1-(4-chlorophenyl)-1H-pyrazolo[3,4-c]pyridin-3-yl]piperidine-2-carboxamide;
1-({1-[1-(4-chlorophenyl)-1H-pyrazolo[3,4-c]pyridin-3-yl]piperidin-2-yl}carbonyl)piperazine;
4-[1-(4-methylphenyl)-1H-pyrrolo[2,3-c]pyridin-3-yl]morpholine;
1-(4-chlorophenyl)-3-(piperidin-4-yl)-1H-pyrrolo[2,3-c]pyridin-4-ol;
N-butyl-1-(4-chlorophenyl)-N-methyl-1H-pyrazolo[3,4-c]pyridin-3-amine;
1-[4-(fluoromethyl)phenyl]-3-(oxan-4-yl)-1H-pyrazolo[3,4-c]pyridine;
3-({4-[1-(4-chlorophenyl)-1H-pyrazolo[3,4-c]pyridin-3-yl]piperidin-1-yl}methyl)pyridine;
and pharmaceutically acceptable salts thereof.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in an amorphous form and/or several polymorphic forms and may be obtained in different crystal habits. Any reference herein, including the claims herein, to "compounds with which the invention is concerned" or "compounds of the invention" or "the present compounds", and the like, includes reference to the compounds irrespective of amorphous or polymorphic form.

DEFINITIONS

The following definitions shall apply throughout the specification and the appended claims, unless otherwise stated or indicated.

As used herein, the term "compound of the invention" refers to the 30 compounds listed above, and includes their pharmaceutically acceptable salts, hydrates, and solvate.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., *The Organic Chem-* istry of Drug Design and Drug Action, 2$^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Tautomers include enol and keto forms. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of the invention may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

In one aspect, the invention relates to a compound of the invention for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders, or inhibition of tumour growth.

In particular, it is believed that the compounds of the invention are useful for the treatment or prevention of arthritis (such as rheumatoid arthritis, juvenile rheumatoid arthritis, osteoarthritis and psoriatic arthritis), synovitis, vasculitis, conditions associated with inflammation of the bowel (such as Crohn's disease, ulcerative colitis, inflammatory bowel disease and irritable bowel syndrome), atherosclerosis, multiple sclerosis, Alzheimer's disease, vascular dementia, pulmonary inflammatory diseases (such as asthma, chronic obstructive pulmonary disease and acute respiratory distress syndrome), fibrotic diseases (including idiopathic pulmonary fibrosis, cardiac fibrosis and systemic sclerosis (scleroderma)), inflammatory diseases of the skin (such as contact dermatitis, atopic dermatitis and psoriasis), systemic inflammatory response syndrome, sepsis, inflammatory and/or autoimmune conditions of the liver (such as autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, ischemic diseases (such as stroke and ischemia-reperfusion injury), and myocardial infarction and/or the complications thereof.

It is believed that the compounds of the invention are especially useful for the treatment or prevention of vasculitis, including, but not limited to, giant cell arteritis, Takayasu's arteritis, Polyarteritis nodosa, Kawasaki disease, Wegener's granulomatosis, Churg-Strauss syndrome, microscopic polyangiitis, Henoch-Schönlein purpura, cryoglobulinemia, cutaneous leukocytoclastic angiitis and primary angiitis of the central nervous system.

It is also believed that the compounds of the invention are especially useful for the treatment of rheumatoid arthritis, chronic obstructive pulmonary disease or atopic dermatitis.

In view of the evidence cited in the above introduction that VAP1 is up regulated in several cancers, including gastric cancer, melanoma, hepatoma and head and neck tumours and that mice bearing enzymatically inactive VAP-1 grow melanomas more slowly, and in view of the link between VAP1 and angiogenesis, it is also expected that the compounds of the invention are anti-angiogenic and therefore have utility in the treatment of cancers by inhibition of tumour growth.

The invention thus includes the compounds of the invention for use in the treatment or prevention of the above-mentioned conditions and diseases. The invention also includes the use of said compounds in the manufacture of a medicament for the treatment or prevention of the above-mentioned conditions and diseases. The invention furthermore includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

COMPOSITIONS

A currently preferred embodiment of the invention is a pharmaceutical composition comprising a compound of the invention, together with one or more pharmaceutically acceptable carriers and/or excipients.

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of the invention may be prepared by, or in analogy with, conventional methods. The preparation of intermediates and compounds according to the examples of the present invention may in particular be illuminated by the following Schemes. Definitions of variables in the structures in schemes herein are commensurate with those of corresponding positions in the formulas delineated herein.

Scheme 1. General synthetic routes for preparation of compounds of formula (Ia)

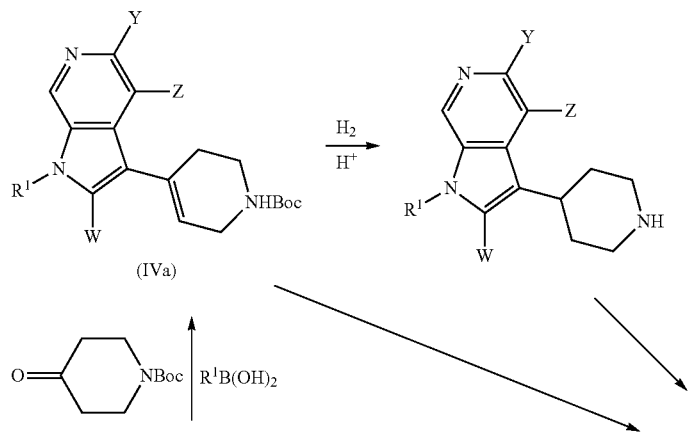

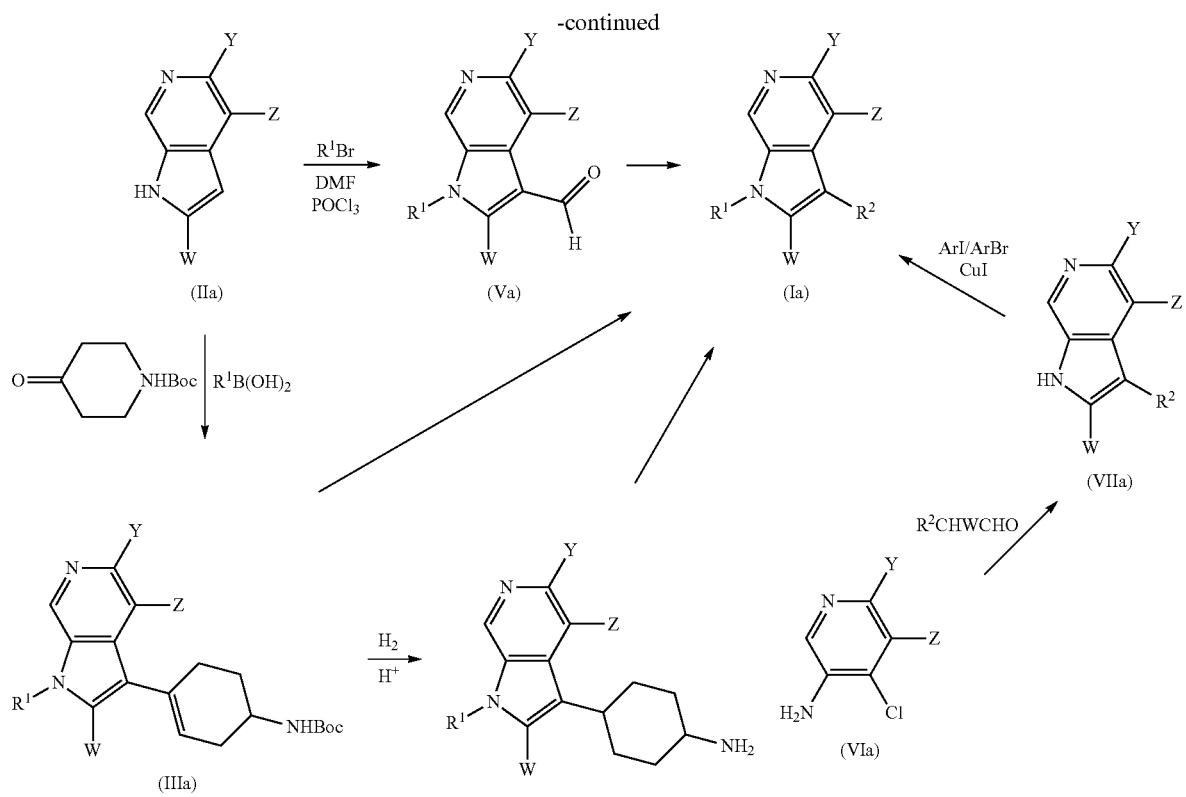

wherein W, Y, Z, $R^1$ and $R^2$ are as defined in formula (I);

Compounds of general formula (Ia) can easily be prepared from 1H-pyrrolo[2,3-c]pyridines (IIa) by either reaction with a ketone to introduce a functional group at $R^2$ followed by introduction of $R^1$ (for example by a Suzuki reaction) to give compounds of formula (IIIa/IVa), or by initial introduction of $R^1$ followed by introduction of a functional group at $R^2$ that can be modified to give alternative $R^2$, as in (Va). Compounds of formulae (IIIa), (IVa) and (Va) can easily be converted into compounds of general formula (Ia) by standard synthetic methods. Alternatively, 4-Chloro-3-aminopyridines (VIa) can be cyclised with the appropriate aldehyde to give compounds of general formula (VIIa) followed by introduction of $R^1$ (for example by an arylation reaction). The latter approach is known to those skilled in the art, for example in Xu et al., Synthesis, 24, 3981-3987, 2008.

Scheme 2. General synthetic route for preparation of compounds of formula (Ic).

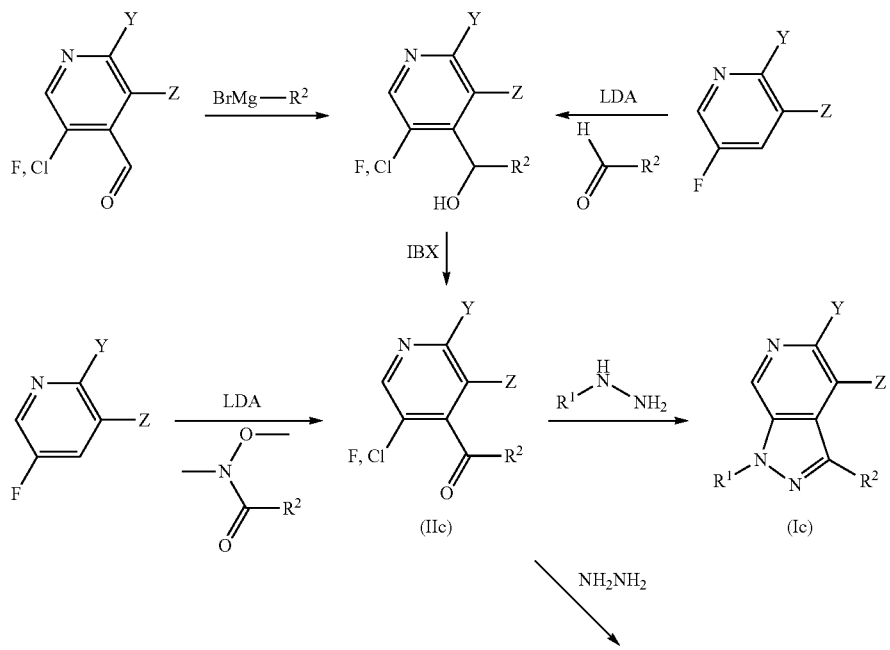

-continued

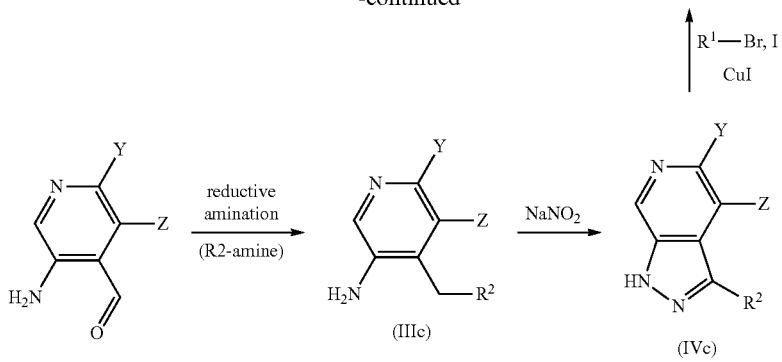

(IIIc) (IVc)

wherein Y, Z, $R^1$, $R^2$ and $R^3$ are as defined in formula (I);

Compounds of general formula (Ic) can easily be prepared according to standard methods known in the scientific literature, for example, by the cyclisation of 3-halo-4-[(pyridin-4-yl)carbonyl compounds of general formula (IIc) with hydrazines, or by cyclisation of compounds of general formula (IIIc) to give compounds of general formula (IVc), and subsequent introduction of $R^1$ (for example by an arylation reaction). Such methods are known to those skilled in the art, for example in Verma et al, Tet. Lett., 50, 383, 2009 and Zhu et al., BioOrg. Med. Chem. Lett., 15, 2441-2452, 2007.

Optionally, a compound of formula (I) can also be transformed into another compound of formula (I) in one or more synthetic steps.

The following abbreviations have been used:
Ac acetyl
$Ac_2O$ Acetic anhydride
AcOH acetic acid
aq aqueous
Ar aryl
Boc tert-butoxycarbonyl
nBuLi n-butyllithium
calcd calculated
cat catalytic
CDI carbonyldiimidazole
conc concentrated
d day
DCE dichloroethane
DCM dichloromethane
DIBALH Diisobutylaluminium hydride
DIPEA diisopropylethylamine
DMAP 4-dimethylaminopyridine
DMF dimethylformamide
EDC 1-ethyl-3-(3-dimethylaminopropyl)carbodiimide hydrochloride
ES+ electrospray ionization
EtOAc ethyl acetate
EtOH ethanol
h hour(s)
HBTU O-benzotriazole-N,N,N',N-tetramethyl-uronium-hexafluoro-phosphate
HOBt 1-hydroxybenzotriazole hydrate
HPLC High Performance Liquid Chromatography
HRMS High-Resolution Mass Spectrometry
IBX 2-Iodoxybenzoic acid
Int Intermediate
LCMS Liquid Chromatography Mass Spectrometry
LDA lithium diisopropylamide
M molar
Me methyl
MeCN Acetonitrile
MeOH methanol
min minute(s)
MS Mass Spectrometry
$NaBH(OAc)_3$ sodium triacetoxyborohydride
NBS N-bromosuccinimide
NIS N-iodosuccinimide
NMP N-methylpyrrolidone
Ph phenyl
PhMe toluene
Rf Retention time
RT room temperature
sat saturated
SCX Strong Cation Exchange
SM starting material
TFA trifluoroacetic acid
THF tetrahydrofuran

EXAMPLES AND INTERMEDIATE COMPOUNDS

Experimental Methods

Reactions were conducted at room temperature unless otherwise specified. Microwave reactions were performed with a Biotage microwave reactor using process vials fitted with aluminum caps and septa. Hydrogenations were performed using a Thales H-Cube. Preparative flash chromatography was performed on Merck silica gel 60 (230-400 mesh) or using a Flash Master Personal system equipped with Strata SI-1 silica gigatubes, or using a CombiFlash Companion system equipped with RediSep silica columns. Reverse phase column chromatography was performed on a Gilson system (Gilson 321 pump and Gilson FC204 fraction collector) equipped with Merck LiChroprep® RP-18 (40-63 um) columns. Reverse Phase HPLC was performed on a Gilson system with a UV detector equipped with Phenomenex Synergi Hydro RP 150×10 mm, or YMC ODS-A 100/150×20 mm columns. The purest fractions were collected, concentrated and dried under vacuum. Compounds were typically dried in a vacuum oven at 40° C. prior to purity analysis. Compound analysis was performed by HPLC/LCMS using an Agilent 1100 HPLC system/Waters ZQ mass spectrometer connected to an Agilent 1100 HPLC system with a Phenomenex Synergi, RP-Hydro column (150×4.6 mm, 4 μm, 1.5 mL per min, 30° C., gradient 5-100% MeCN (+0.085% TFA) in water (+0.1% TFA) over 7 min, 200-300 nm). Accurate masses (HRMS) were measured using a Thermo Scientific LTQ Orbitrap XL equipped with an Advio TriVersa NanoMate electrospray ion source (during the analyses the calibration was checked by three masses. Spectra were acquired in positive electrospray mode. The acquired mass range was m/z 100-2000. Samples were dissolved in DMSO to give 10 mM solutions which were then further diluted with MeOH or 10 mM NH$_4$OAc in MeOH to ~0.1M solutions prior to analysis). The values reported correspond to the protonated molecular ions (MH+). The compounds prepared were named using ACD Name 6.0, 7.0 or 10.0.

Intermediate 1 tert-Butyl 4-{1H-pyrrolo[2,3-c]pyridin-3-yl}-1,2,3,6-tetrahydropyridine-1-carboxylate

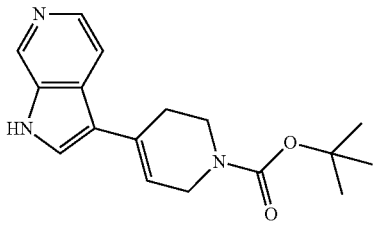 [SMILES: CC(C)(C)OC(=O)N1CC=C(c2c[nH]c3cnccc23)CC1]

6-Azaindole (4.48 g, 37.9 mmol) was dissolved in MeOH (70 mL) and KOH (4.68 g, 83.4 mmol) and tert-butyl 4-oxopiperidine-1-carboxylate (8.31 g, 41.7 mmol) were added. The reaction mixture was heated at 70° C. for 18 h. The residue was partitioned between water (250 mL) and DCM (250 mL) and the aq phase was extracted with DCM (2×250 mL). The combined organic fractions were dried (MgSO$_4$) and concentrated in vacuo to give the title compound as a yellow foam (11.3 g, 99%). LCMS (ES+): 300.1 [MH]$^+$.

Intermediate 2 tert-Butyl 4-{1H-pyrrolo[2,3-c]pyridin-3-yl}piperidine-1-carboxylate

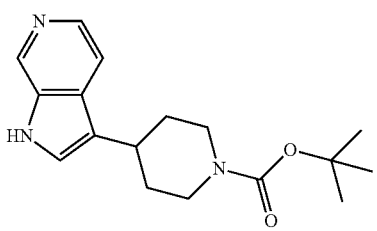 [SMILES: CC(C)(C)OC(=O)N1CCC(c2c[nH]c3cnccc23)CC1]

Intermediate 1 (11.3 g, 37.7 mmol) was dissolved in EtOH (200 mL) and hydrogenated over 10% Pd/C in an H-cube at 90° C. and 90 bar. The reaction mixture was concentrated in vacuo to give the title compound as a yellow solid (11.1 g, 97%). LCMS (ES+): 302.1 [MH]$^+$.

Intermediate 3 tert-Butyl 4-[1-(4-chlorophenyl)-1H-pyrrolo[2,3-c]pyridin-3-yl]piperidine-1-carboxylate

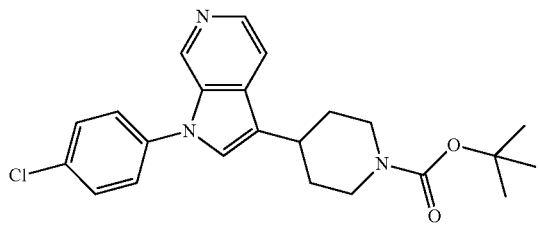 [SMILES: CC(C)(C)OC(=O)N1CCC(c2cn(-c3ccc(Cl)cc3)c3cnccc23)CC1]

Intermediate 2 (11.1 g, 36.7 mmol) was dissolved in DMF (60 mL) and 1-chloro-4-iodobenzene (10.5 g, 44.0 mmol), N,N'-dimethylethylenediamine (789 μL, 7.33 mmol), K$_3$PO$_4$ (16.3 g, 77.0 mmol) and CuI (698 mg, 3.67 mmol) were added under nitrogen. The reaction mixture was heated in a microwave at 160° C. for 20 min and concentrated in vacuo. The residue was partitioned between water (250 mL) and DCM (250 mL) and the aq phase was extracted with DCM (2×250 mL). The combined organic fractions were dried (MgSO$_4$) and concentrated in vacuo. The residue was purified by column chromatography to give the title compound as a yellow solid (6.86 g, 45%). LCMS (ES+): 411.9 [MH]$^+$, HPLC: Rf 5.91 min, 76% purity.

Intermediate 4

4-[1-(4-Chlorophenyl)-1H-pyrrolo[2,3-c]pyridin-3-yl]piperidine

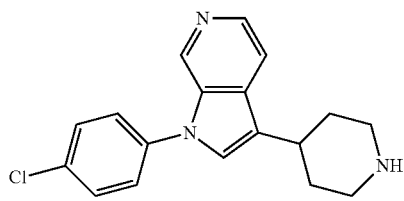 [SMILES: Clc1ccc(-n2cc(C3CCNCC3)c3ccncc32)cc1]

Intermediate 3 (6.86 g, 16.6 mmol) was dissolved in DCM (200 mL) and TFA (50 mL) and stirred for 2 h. The solvents were removed in vacuo and the residue was dissolved in 1 M aq Na$_2$CO$_3$ (200 mL) and extracted with DCM (3×200 mL).

The combined organic fractions were dried (MgSO$_4$) and concentrated in vacuo. The residue was purified by column chromatography to give the title compound as a red gum (3.18 g, 61%). LCMS (ES$^+$): 312.1 [MH]$^+$. HPLC: Rf 3.61 min, 96% purity.

Intermediate 5

Ethyl 1-[(3-aminopyridin-4-yl)methyl]piperidine-4-carboxylate

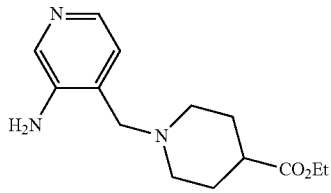 [SMILES: CCOC(=O)C1CCN(Cc2ccncc2N)CC1]

3-Amino-pyridine-4-carbaldehyde (5.00 g, 40.9 mmol) was dissolved in DCM (60 mL), ethyl 4-piperidinecarboxylate (7.57 mL, 49.1 mmol) and NaBH(OAc)$_3$ (10.4 g, 49.1 mmol) were added and the reaction mixture was heated in a microwave reactor at 60° C. for 5 min. The reaction mixture was diluted with DCM (100 mL) and quenched with sat aq Na$_2$CO$_3$ (50 mL). The organic fraction was washed with sat aq NH$_4$Cl (30 mL). The combined aq fractions were extracted with DCM (2×50 mL) and the combined organic fractions were dried (MgSO$_4$) and concentrated in vacuo to give the crude title compound as a yellow gum (11.3 g). LCMS (ES$^+$): 264.1 [MH]$^+$.

Intermediates 6 to 12

Intermediates 6-12 were prepared similarly to Intermediate 5, by reductive amination of 3-amino-pyridine-4-carbaldehyde with the appropriate amine; see Table 1 below.

TABLE 1

Reductive aminations of 3-amino-pyridine-4-carbaldehyde

| Int | Structure | Crude yield | LCMS (ES$^+$) | Intermediate Name |
|---|---|---|---|---|
| 6 | 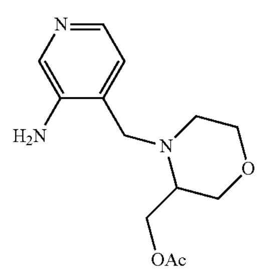 [SMILES: CC(=O)OCC1COCCN1Cc1ccncc1N] | 2.88 g 48% | 266.1 [MH]$^+$ | {4-[(3-Aminopyridin-4-yl)methyl]morpholin-3-yl}methyl acetate |
| 7 | 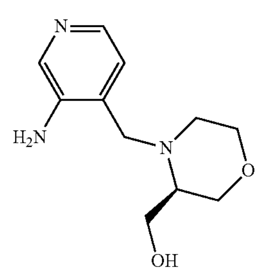 [SMILES: Nc1cnccc1CN1CCOC[C@H]1CO] | 666 mg 14% | 224.0 [MH]$^+$ | [(3R)-4-[(3-Aminopyridin-4-yl)methyl]morpholin-3-yl]methanol |
| 8 | 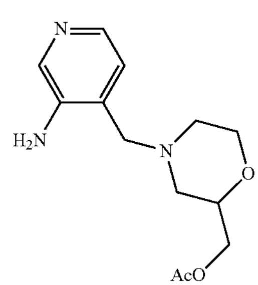 [SMILES: CC(=O)OCC1CN(Cc2ccncc2N)CCO1] | 5.77 g 44% | 266.1 [MH]$^+$ | {4-[(3-Aminopyridin-4-yl)methyl]morpholin-2-yl}methyl acetate |

TABLE 1-continued

Reductive aminations of 3-amino-pyridine-4-carbaldehyde

| Int | Structure | Crude yield | LCMS (ES+) | Intermediate Name |
|---|---|---|---|---|
| 9 | 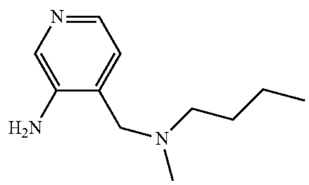 | 673 mg 85% | 194.1 [MH]+ | 4-{Butyl(methyl)amino]methyl} pyridin-3-amine |
| 10 | 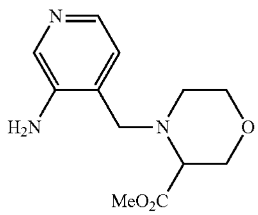 [SMILES: COC(=O)C1COCCN1Cc1ccncc1N] | 2.43 g 99% | 252.1 [MH]+ | Methyl 4-[(3-aminopyridin-4-yl)methyl]morpholine-3-carboxylate |
| 11 | 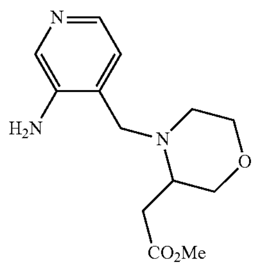 [SMILES: COC(=O)CC1COCCN1Cc1ccncc1N] | 3.16 g 63% | 266.1 [MH]+ | Methyl 2-{4-[(3-aminopyridin-4-yl)methyl]morpholin-3-yl}acetate |
| 12 | 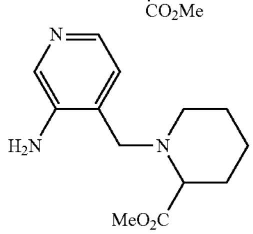 | 1.76 g 40% | 250.1 [MH]+ | Methyl 1-[(3-aminopyridin-4-yl)methyl]piperidine-2-carboxylate |

Intermediate 13

Ethyl 1-{1H-pyrazolo[3,4-c]pyridin-3-yl}piperidine-4-carboxylate

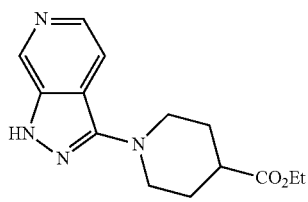 [SMILES: CCOC(=O)C1CCN(c2n[nH]c3cnccc23)CC1]

Intermediate 5 (6.81 g, 25.9 mmol) was dissolved in AcOH (334 mL), cooled to 0° C. and a solution of NaNO₂ (1.78 g, 25.9 mmol) in water (2.72 mL) was added. The reaction mixture was stirred at 0° C. for 5 min and concentrated in vacuo. The residue was dissolved in EtOAc (200 mL), washed with sat aq Na₂CO₃ (2×100 mL), dried (MgSO₄) and concentrated in vacuo to give the crude title compound as a brown gum (12.2 g). LCMS (ES+): 275.1 [MH]+.

Intermediates 14 to 20

Intermediates 14-20 were prepared similarly to Intermediate 13, by cyclisation of Intermediates 6-12 with NaNO₂; see Table 2 below.

TABLE 2

Cyclisation of 3-aminopyidines

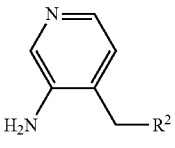

| Int | Structure | SM/ Crude yield | LCMS (ES+) | Intermediate Name |
|---|---|---|---|---|
| 14 | 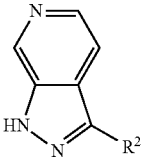 | Int 6 1.73 g 58% | 277.1 [MH]+ | (4-{1H-Pyrazolo[3,4-c]pyridin-3-yl}morpholin-3-yl)methyl acetate |
| 15 | 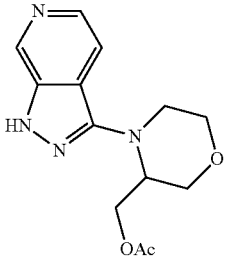 [SMILES: CC(=O)OCC1COCCN1c1n[nH]c2cnccc12] | Int 7 194 mg 65% | 235.1 [MH]+ | [(3R)-4-{1H-Pyrazolo[3,4-c]pyridin-3-yl}morpholin-3-yl]methanol |
| 16 | 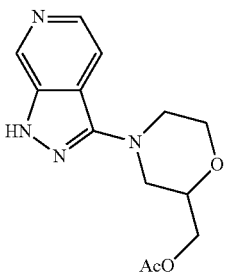 [SMILES: CC(=O)OCC1CN(c2n[nH]c3cnccc23)CCO1] | Int 8 3.85 g 64% | 277.1 [MH]+ | (4-{1H-Pyrazolo[3,4-c]pyridin-3-yl}morpholin-2-yl)methyl acetate |
| 17 | 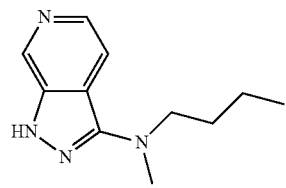 | Int 9 622 mg 88% | 205.1 [MH]+ | N-Butyl-N-methyl-1H-pyrazolo[3,4-c]pyridin-3-amine |
| 18 | 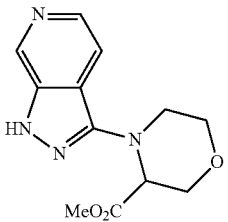 [SMILES: COC(=O)C1COCCN1c1n[nH]c2cnccc12] | Int 10 1.97 g 74% | 263.0 [MH]+ | Methyl 4-{1H-pyrazolo[3,4-c]pyridin-3-yl}morpholine-3-carboxylate |

TABLE 2-continued

Cyclisation of 3-aminopyridines

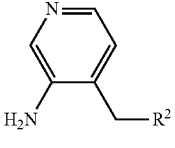

| Int | Structure | SM/Crude yield | LCMS (ES⁺) | Intermediate Name |
|---|---|---|---|---|
| 19 | 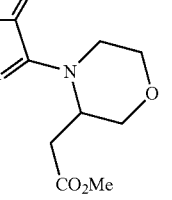 | Int 11<br>2.00 g<br>100% | 277.1 [MH]⁺ | 2-(4-{1H-Pyrazolo[3,4-c]pyridin-3-yl}morpholin-3-yl)acetate |
| 20 | 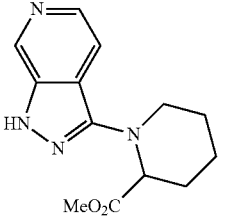 [SMILES: COC(=O)C1CCCCN1c1n[nH]c2cnccc12] | Int 12<br>650 g<br>89% | 261.1 [MH]⁺ | Methyl 1-{1H-pyrazolo[3,4-c]pyridin-3-yl}piperidine-2-carboxylate |

Intermediates 21 to 22

Intermediates 21-22 were prepared similarly to Intermediate 3, by N-arylation of 1H-pyrazolo[3,4-c]pyridines; see Table 3 below.

TABLE 3

N-Arylation of 1H-pyrazolo[3,4-c]pyridines

| Int | Structure | SM/Crude yield | LCMS (ES⁺) | Intermediate Name |
|---|---|---|---|---|
| 21 | 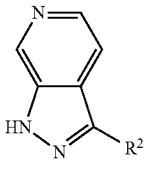 | Int 14<br>51.0 mg<br>2% | 367.0 [MH]⁺ | {4-[1-(4-Methylphenyl)-1H-pyrazolo[3,4-c]pyridin-3-yl]morpholin-3-yl}methyl acetate |

TABLE 3-continued

N-Arylation of 1H-pyrazolo[3,4-c]pyridines

| Int | Structure | SM/Crude yield | LCMS (ES+) | Intermediate Name |
|---|---|---|---|---|
| 22 | 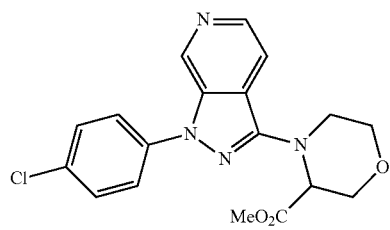 [SMILES: COC(=O)C1COCCN1c1nn(-c2ccc(Cl)cc2)c2cnccc12] | Int 16 260 mg 5% | 367.0 [MH]+ | {4-[1-(4-Methylphenyl)-1H-pyrazolo[3,4-c]pyridin-3-yl]morpholin-2-yl}methyl acetate |

Intermediate 23

Methyl 4-[1-(4-chlorophenyl)-1H-pyrazolo[3,4-c]pyridin-3-yl]morpholine-3-carboxylate Intermediate 18 (1.98 g, 7.53 mmol), 4-chlorophenylboronic acid (2.36 g, 15.1 mmol), $Cu(OAc)_2$ (2.74 g, 15.1 mmol) and pyridine (3.03 mL, 37.7 mmol) were suspended in DCE (52 mL) and stirred overnight. The reaction mixture was purified by column chromatography to give the title compound as a dark yellow solid (552 mg, 20%). LCMS (ES+): 373.2 [MH]+. HPLC: Rf 5.23 min, 98.0% purity.

Intermediate 24

Methyl 2-{4-[1-(4-chlorophenyl)-1H-pyrazolo[3,4-c]pyridin-3-yl]morpholin-3-yl}acetate

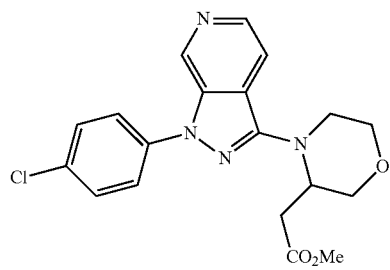 [SMILES: COC(=O)CC1COCCN1c1nn(-c2ccc(Cl)cc2)c2cnccc12]

Intermediate 19 (1.64 g, 5.94 mmol), 4-chlorophenylboronic acid (1.86 g, 11.9 mmol), $Cu(OAc)_2$ (2.16 g, 11.9 mmol) and pyridine (2.39 mL, 29.7 mmol) were suspended in DCE (41 mL) and stirred overnight. The reaction mixture was purified by column chromatography to give the title compound as a yellow gum (866 mg, 38%). LCMS (ES+): 387.3 [MH]+. HPLC: Rf 5.32 min, 100% purity.

Intermediate 25

4-[1-(4-Chlorophenyl)-1H-pyrazolo[3,4-c]pyridin-3-yl]morpholine-3-carboxylic acid hydrochloride

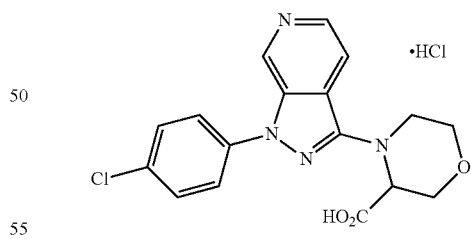

Intermediate 23 (84.0 mg, 0.23 mmol) was dissolved in 1:1 THF/water (2 mL), LiOH/$H_2O$ (20.8 mg, 0.50 mmol) was added and the reaction mixture was stirred for 3 h. The THF was removed in vacuo and the aq residue was acidified to pH 1 with 1 M aq HCl (1 mL) and concentrated in vacuo to give the crude title compound as an orange gum (115 mg). LCMS (ES+): 359.2 [MH]+. HPLC: Rf 4.59 min, 97.1% purity.

Intermediate 26

1-[1-(4-Chlorophenyl)-1H-pyrazolo[3,4-c]pyridin-3-yl]piperidine-2-carboxylic acid hydrochloride

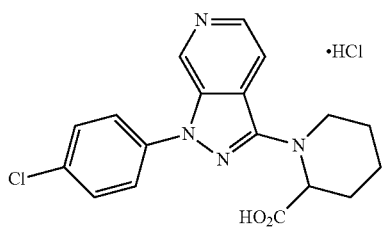 [SMILES: O=C(O)C1CCCCN1c1nn(-c2ccc(Cl)cc2)c2cnccc12 ; Cl]

Intermediate 26 was prepared similarly to Intermediate 25, using Example 23 instead of Intermediate 23, to give the crude title compound as a brown solid (332 mg). LCMS (ES+): 357.0 [MH]+.

Intermediate 27

Methyl 2-(3-nitropyridin-4-yl)acetate

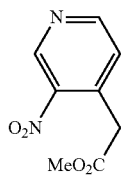

3-Nitropyridine (5.00 g, 40.3 mmol) and methyl chloroacetate (7.30 g, 67.3 mmol) were dissolved in THF (50 mL) and added drop-wise to a slurry of KOtBu (18.1 g, 161 mmol) in THF (50 mL) at 0° C. The reaction mixture was stirred at RT for 1 h, cooled to 0° C. and quenched with sat aq NH4Cl (100 mL). The THF was removed in vacuo and the reaction mixture was diluted with DCM (75 mL). The aq fraction was extracted with DCM (3×40 mL) and the combined organic fractions were washed with brine (100 mL), dried (MgSO4) and concentrated in vacuo. The residue was purified by column chromatography to give the title compound as a dark brown oil (3.94 g, 50%). LCMS (ES+): 196.9 [MH]+.

Intermediate 28

Methyl 2-bromo-2-(3-nitropyridin-4-yl)acetate

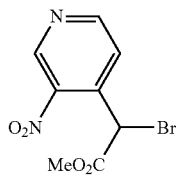

Intermediate 27 (2.66 g, 13.6 mmol), NBS (2.65 g, 14.9 mmol) and azobisisobutyronitrile (66.8 mg, 0.41 mmol) were dissolved in CCl4 (20 mL) and the reaction mixture was heated under reflux for 5 h and concentrated in vacuo. The residue was purified by column chromatography to give the title compound as an orange oil (3.25 g, 87%). LCMS (ES+): 274.3, 276.3 [MH]+.

Intermediate 29

Methyl 2-(morpholin-4-yl)-2-(3-nitropyridin-4-yl)acetate

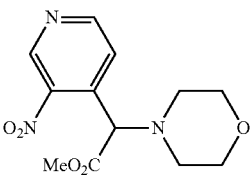 [SMILES: COC(=O)C(c1ccncc1[N+](=O)[O-])N1CCOCC1]

Intermediate 28 (2.00 g, 7.27 mmol) was dissolved in MeCN (30 mL), morpholine (944 µL, 10.9 mmol) was added and the reaction mixture was stirred overnight. The precipitate was removed by filtration and the filtrate was concentrated in vacuo. The residue was purified by normal phase column chromatography to give the title compound as a yellow solid (1.63 g, 80%). LCMS (ES+): 282.0 [MH]+.

Intermediate 30

Methyl 2-(3-aminopyridin-4-yl)-2-(morpholin-4-yl)acetate

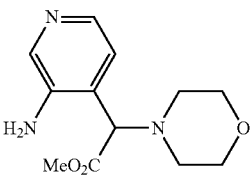

Intermediate 29 (989 mg, 3.52 mmol) was dissolved in EtOAc (33 mL) and MeOH (37 mL) and hydrogenated over 10% Pd/C using a Thales H-cube (55° C., 1 bar). The reaction mixture was concentrated in vacuo to give the crude title compound as a brown oil (916 mg, 100%). LCMS (ES+): 252.0 [MH]+.

Intermediate 31

4-{1H-Pyrrolo[2,3-c]pyridin-3-yl}morpholine

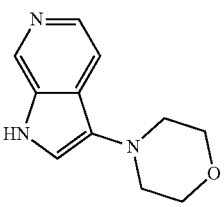 [SMILES: c1cc2c(N3CCOCC3)c[nH]c2cn1]

Intermediate 30 (916 mg, 3.65 mmol) was dissolved in THF (10 mL), cooled to −78° C. and LiAlH4 (2.28 mL, 2.4 M in THF, 5.47 mmol) was added. The reaction mixture was stirred at −78° C. for 1 h, further LiAlH4 (759 µL, 2.4 M in THF, 1.82 mmol) was added and the reaction mixture was stirred at −78° C. for 1 h. The reaction mixture was quenched with 1 M aq NaOH, filtered through celite and concentrated in vacuo. The residue was purified by normal phase column chromatography to give the title compound (517 mg, 70%) as a pale yellow gum. LCMS (ES+): 204.0 [MH]+.

Intermediate 32

3-Iodo-4-methoxy-1H-pyrrolo[2,3-c]pyridine

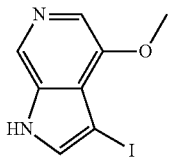

4-Methoxy-6-azaindole (662 mg, 4.47 mmol) was dissolved in CHCl₃ (20 mL), NIS (1.06 g, 4.69 mmol) was added and the reaction mixture was stirred for 18 h. The precipitate was collected by filtration and the filtrate was concentrated in vacuo. The residue was dissolved in EtOAc (50 mL), washed with 10% aq sodium thiosulfate (50 mL), sat aq NaHCO₃ (50 mL) and water (50 mL), dried (MgSO₄), concentrated in vacuo and combined with the precipitate to give the title compound as a red solid (1.12 g, 91%). LCMS (ES+): 274.9 [MH]+. HPLC: Rf 3.98 min, 96% purity.

Intermediate 33

1-{3-Iodo-4-methoxy-1H-pyrrolo[2,3-c]pyridin-1-yl}ethan-1-one

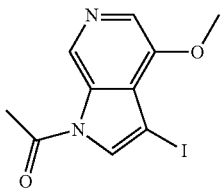

Intermediate 32 (1.12 g, 4.09 mmol) was dissolved in DCM (30 mL) and DMAP (49.9 mg, 0.41 mmol), DIPEA (710 µL, 4.09 mmol) and Ac₂O (424 µL, 4.50 mmol) were added. The reaction mixture was stirred for 18 h, diluted with DCM (100 mL), washed with 1 M aq Na₂CO₃ (100 ml) and water (100 mL), dried (MgSO₄) and concentrated in vacuo to give the title compound as an orange solid (1.25 g, 97%). LCMS (ES+): 316.9 [MH]+. HPLC: Rf 3.92 min, 97% purity.

Intermediate 34 tert-Butyl 4-{4-methoxy-1H-pyrrolo[2,3-c]pyridin-3-yl}-1,2,3,6-tetrahydro pyridine-1-carboxylate

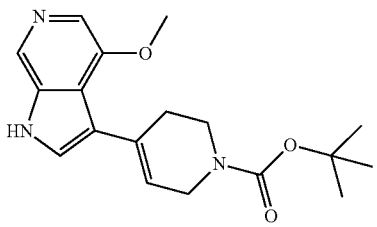 [SMILES: COc1cncc2[nH]cc(C3=CCN(C(=O)OC(C)(C)C)CC3)c12]

Intermediate 33 (1.14 g, 3.61 mmol), tert-butyl 4-(4,4,5,5-tetramethyl-1,3,2-dioxaborolan-2-yl)-1,2,3,6-tetrahydropyridine-1-carboxylate (1.12 g, 3.61 mmol) and Na₂CO₃ (1.15 g, 10.8 mmol) were dissolved in dioxane (15 mL) and water (3 mL) and Pd(PPh₃)₄ (624 mg, 0.54 mmol) was added. The reaction mixture was heated at 100° C. in a microwave reactor for 2 h, diluted with water (100 mL) and extracted with DCM (2×100 mL) and EtOAc (2×100 mL). The combined organic fractions were dried (MgSO₄), concentrated in vacuo and purified by column chromatography to give the title compound as a yellow solid (502 mg, 37%). LCMS (ES+): 330.0 [MH]+.

Intermediate 35 tert-Butyl 4-{4-methoxy-1H-pyrrolo[2,3-c]pyridin-3-yl}piperidine-1-carboxylate

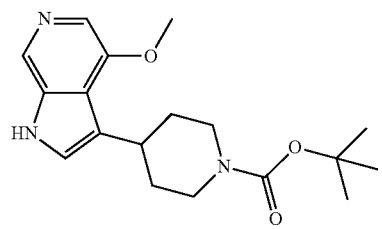 [SMILES: COc1cncc2[nH]cc(C3CCN(C(=O)OC(C)(C)C)CC3)c12]

Intermediate 35 was prepared similarly to Intermediate 2, using Intermediate 34 instead of Intermediate 1, to give the title compound as a yellow gum (260 mg, 51%). LCMS (ES+): 332.1 [MH]+.

Intermediate 36 tert-Butyl 4-[1-(4-chlorophenyl)-4-methoxy-1H-pyrrolo[2,3-c]pyridin-3-yl]piperidine-1-carboxylate

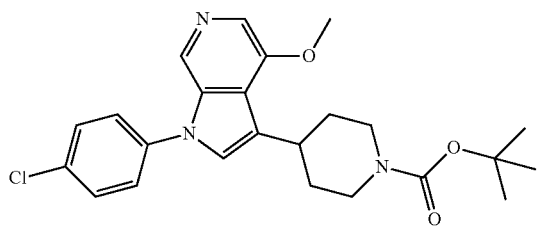 [SMILES: COc1cncc2c1c(C1CCN(C(=O)OC(C)(C)C)CC1)cn2-c1ccc(Cl)cc1]

Intermediate 36 was prepared similarly to Intermediate 3, using Intermediate 35 instead of Intermediate 2, to give the title compound as a yellow solid (141 mg, 41%). LCMS (ES+): 442.0 [MH]+.

Intermediate 37

N-Methoxy-N-methyloxane-4-carboxamide

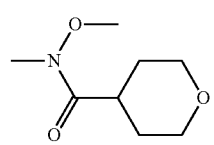

N,O-Dimethylhydroxylamine hydrochloride (1.23 g, 12.7 mmol) and N-methyl morpholine (3.80 mL, 34.5 mmol) were dissolved in DCM (20 mL) and a solution of oxane-4-carbonyl chloride (1.71 g, 11.5 mmol) in DCM (20 mL) was added drop-wise. The reaction mixture was stirred for 2 h, then diluted to 200 mL with DCM, washed with 1 M aq HCl (2×100 mL), 1M aq Na₂CO₃ (100 mL) and water (100 mL), dried (MgSO$_4$) and concentrated in vacuo to give the crude title compound as a yellow oil (1.87 g, 94%). LCMS (ES$^+$): 174.1 [MH]$^+$.

Intermediate 38

3-Fluoro-4-[(oxan-4-yl)carbonyl]pyridine

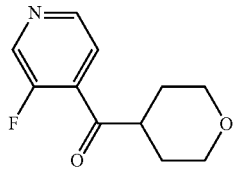 [SMILES: O=C(c1ccncc1F)C1CCOCC1]

Diisopropylamine (1.50 ml, 10.8 mmol) was dissolved in THF (30 mL) and cooled to −78° C. under nitrogen. nBuLi (4.32 mL, 2.5 M in hexanes, 10.8 mmol) was added drop-wise and the resulting solution was stirred at −78° C. for 10 min, at 0° C. for 30 min and then re-cooled to −78° C. 3-Fluoro-pyridine (0.93 mL, 10.8 mmol) was added drop-wise over 5 min and the reaction mixture was stirred for 2 h. A solution of Intermediate 37 (1.87 g, 10.8 mmol) in THF (15 mL) was added and the reaction mixture was allowed to warm to RT and stirred for 15 min. The reaction mixture was quenched with sat aq NH$_4$OAc (10 mL) and diluted with EtOAc (200 mL). The organic fraction was washed with water (2×50 mL), dried (MgSO$_4$) and concentrated in vacuo to give the crude title compound as an orange oil (1.45 g, 64%). LCMS (ES$^+$): 210.1 [MH]$^+$.

Intermediate 39

3-(Oxan-4-yl)-1H-pyrazolo[3,4-c]pyridine

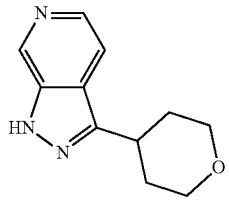

Intermediate 38 (255 mg, 1.22 mmol) and hydrazine monohydrate (134 mg, 2.68 mmol) were dissolved in NMP (3 mL) and the reaction mixture was heated in a microwave at 160° C. for 20 min. The reaction mixture was purified by SCX to give the title compound as an orange oil (245 mg, 99%). LCMS (ES$^+$): 204.1 [MH]$^+$.

Intermediate 40 tert-Butyl 4-[(3-fluoropyridin-4-yl)(hydroxy)methyl]piperidine-1-carboxylate

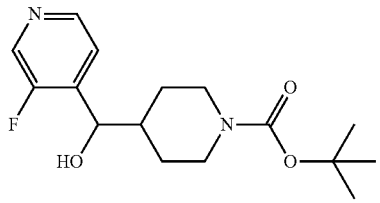 [SMILES: CC(C)(C)OC(=O)N1CCC(C(O)c2ccncc2F)CC1]

Diisopropylamine (0.66 ml, 4.69 mmol) was dissolved in THF (30 ml) and cooled to −78° C. nBuLi (2.13 ml, 2.20 M in cyclohexane, 4.69 mmol) was added drop-wise and the reaction mixture was stirred at −78° C. for 10 min, at 0° C. for 30 min, and re-cooled to −78° C. 3-Fluoro-pyridine (0.40 ml, 4.69 mmol) was added drop-wise over 5 min, and the reaction mixture was stirred for 45 min. A solution of N-Boc-4-piperidinecarboxaldehyde (1.00 g, 4.69 mmol) in THF (10 ml) was added and the reaction mixture was warmed to RT and stirred for 15 min. The reaction mixture was quenched with sat aq NH$_4$OAc (10 mL), diluted with EtOAc (100 mL), washed with water (2×50 mL), dried (MgSO$_4$) and concentrated in vacuo to give the title compound as an orange oil (1.42 g, 98%). LCMS (ES$^+$): 255.0 [MH-t-Bu]$^+$.

Intermediate 41 tert-Butyl 4-[(3-fluoropyridin-4-yl)carbonyl]piperidine-1-carboxylate

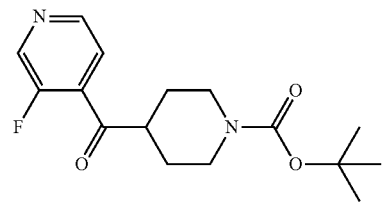 [SMILES: CC(C)(C)OC(=O)N1CCC(C(=O)c2ccncc2F)CC1]

Intermediate 40 (1.42 g, 4.58 mmol) and IBX (1.93 g, 6.88 mmol) were dissolved in DCE (30 mL) and the reaction mixture was stirred at 65° C. for 16 h. The reaction mixture was cooled and filtered and the filtrate was concentrated in vacuo to give the crude title compound (1.96 g) as a yellow liquid. LCMS (ES$^+$): 209.1 [MH-Boc]$^+$.

Intermediate 42 tert-Butyl 4-{1H-pyrazolo[3,4-c]pyridin-3-yl}piperidine-1-carboxylate

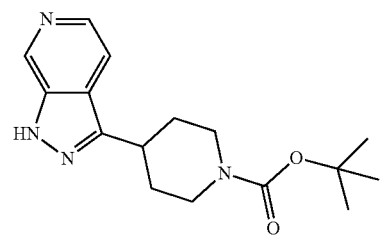 [SMILES: CC(C)(C)OC(=O)N1CCC(c2n[nH]c3cnccc23)CC1]

Intermediate 41 (1.42 g, 4.61 mmol) and hydrazine monohydrate (407 μl, 8.31 mmol) were dissolved in NMP (5 mL) and the reaction mixture was heated in a microwave reactor at 160° C. for 20 min and purified by SCX and column chromatography to give the title compound as a orange oil (1.15 g, 83%). LCMS (ES$^+$): 303.1 [MH]$^+$.

Intermediate 43 tert-Butyl 4-[1-(4-chlorophenyl)-1H-pyrazolo[3,4-c]pyridin-3-yl]piperidine-1-carboxylate

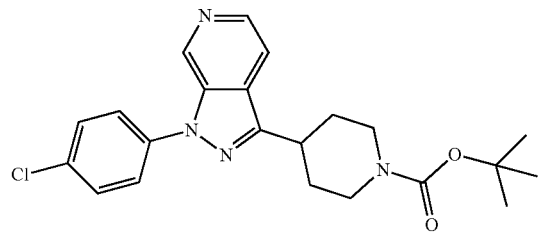 [SMILES: CC(C)(C)OC(=O)N1CCC(c2nn(-c3ccc(Cl)cc3)c3cnccc23)CC1]

Intermediate 43 was prepared similarly to Intermediate 3, using Intermediate 42 instead of Intermediate 2, to give the title compound as a brown gum (1.02 g, 67%). LCMS (ES+): 413.0 [MH]+.

Intermediate 44

4-[1-(4-Chlorophenyl)-1H-pyrazolo[3,4-c]pyridin-3-yl]piperidine

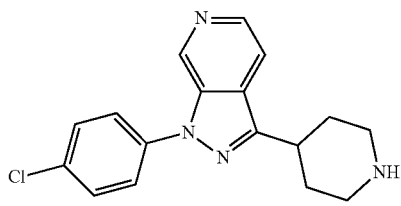 [SMILES: Clc1ccc(-n2nc(C3CCNCC3)c3ccncc32)cc1]

Intermediate 43 (1.02 g, 2.46 mmol) was dissolved in DCM (50 mL) and TFA (10 mL) was added. The reaction mixture was stirred for 1 h, concentrated in vacuo and purified by SCX to give the title compound as a brown oil (696 mg, 90%). LCMS (ES+): 313.0 [MH]+.

Example 1

2,2,2-Trifluoroacetic acid; 2-{4-[1-(4-chlorophenyl)-1H-pyrrolo[2,3-c]pyridin-3-yl]piperidin-1-yl}ethan-1-amine

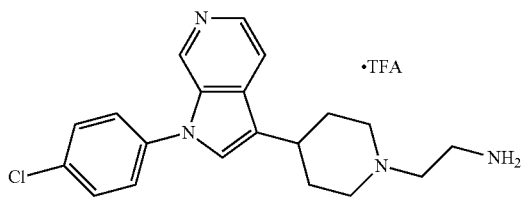 [SMILES: NCCN1CCC(c2cn(-c3ccc(Cl)cc3)c3cnccc23)CC1]

Intermediate 4 (200 mg, 0.64 mmol) was dissolved in DCM (5 mL) and tert-butyl N-(2-oxoethyl)carbamate (203 µL, 1.28 mmol) was added. The reaction mixture was stirred for 1 h and NaBH(OAc)₃ (340 mg, 1.60 mmol) was added. The reaction mixture was stirred for 18 h and partitioned between 1 M aq Na₂CO₃ (50 mL) and DCM (50 mL). The aq phase was extracted with DCM (2×50 mL) and the combined organic fractions were dried (MgSO₄) and concentrated in vacuo. The residue was purified by column chromatography, dissolved in DCM (5 mL) and TFA (1 mL) and stirred for 3 h. The reaction mixture was concentrated in vacuo, dissolved in 1 M aq Na₂CO₃ (50 mL) and extracted with DCM (3×50 mL). The combined organic fractions were dried (MgSO₄) and concentrated in vacuo. The residue was purified by reverse phase HPLC (TFA buffered) to give the title compound as a colourless gum (1.10 mg, 0.4%). HRMS (ESI+) calcd for C20H23ClN4 355.1684. found 355.1687. HPLC: Rf 3.31 min, 97% purity.

Example 2

3-Aminopropyl 4-[1-(4-chlorophenyl)-1H-pyrrolo[2,3-c]pyridin-3-yl]piperidine-1-carboxylate

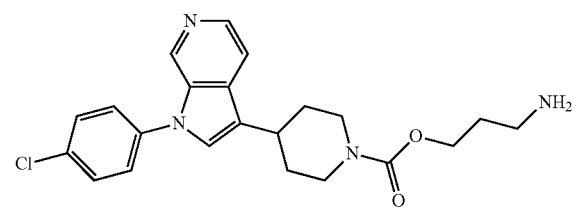 [SMILES: NCCCOC(=O)N1CCC(c2cn(-c3ccc(Cl)cc3)c3cnccc23)CC1]

Triphosgene (119 mg, 0.40 mmol) was dissolved in DCM (5 mL) and a solution of tert-butyl N-(3-hydroxypropyl)carbamate (211 mg, 1.20 mmol) and DIPEA (209 µL, 1.20 mmol) in DCM (1 mL) was added. The reaction mixture was stirred for 3 h and a solution of Intermediate 4 (250 mg, 0.80 mmol) and DIPEA (209 µL, 1.20 mmol) in DCM (1 mL) was added. The reaction mixture was stirred for 3 d, diluted with EtOAc (50 mL) and washed with 10% aq citric acid (50 mL) and 1 M aq Na₂CO₃ (50 mL), dried (MgSO₄) and concentrated in vacuo. The residue was purified by column chromatography, dissolved in DCM (20 mL) and TFA (5 mL) and stirred for 2 h. The reaction mixture was concentrated in vacuo, dissolved in 1 M aq Na₂CO₃ (50 mL) and extracted with DCM (3×50 mL). The combined organic fractions were concentrated in vacuo and the residue was purified by column chromatography to give the title compound as a colourless gum (52.0 mg, 16%). HRMS (ESI+) calcd for C22H25ClN4O2 413.1739. found 413.1739. HPLC: Rf 3.96 min, 98% purity.

Example 3

1-{4-[1-(4-Chlorophenyl)-1H-pyrrolo[2,3-c]pyridin-3-yl]piperidin-1-yl}-4-(dimethylamino)butan-1-one; 2,2,2-trifluoroacetic acid

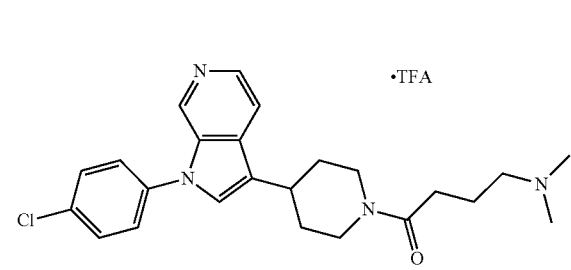 [SMILES: CN(C)CCCC(=O)N1CCC(c2cn(-c3ccc(Cl)cc3)c3cnccc23)CC1]

Intermediate 4 (200 mg, 0.64 mmol), 4-(dimethylamino)butanoic acid hydrochloride (140 mg, 0.83 mmol), HOBt (113 mg, 0.83 mmol) and DIPEA (290 µL, 1.67 mmol) were dissolved in DMF (5 mL) and EDC (160 mg, 0.83 mmol) was added. The reaction mixture was stirred for 18 h and concentrated in vacuo. The residue was dissolved in 1 M aq Na₂

CO₃ (50 mL) and extracted with DCM (3×50 mL). The combined organic fractions were dried (MgSO₄) and concentrated in vacuo. The residue was purified by column chromatography and reverse phase HPLC (TFA buffered) to give the title compound as a colourless gum (37.0 mg, 11%). HRMS (ESI+) calcd for C24H29ClN4O, 425.2103. found 425.2109. HPLC: Rf 4.00 min, 98% purity.

Example 4

5-Amino-1-{4-[1-(4-chlorophenyl)-1H-pyrrolo[2,3-c]pyridin-3-yl]piperidin-1-yl}pentan-1-one

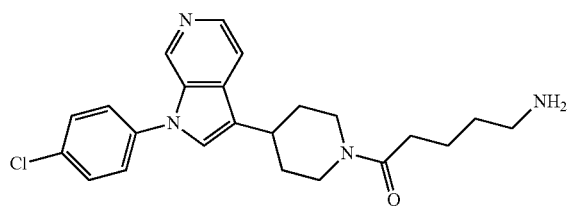 [SMILES: NCCCCC(=O)N1CCC(c2cn(-c3ccc(Cl)cc3)c3cnccc23)CC1]

Intermediate 4 (200 mg, 0.64 mmol) was dissolved in DMF (10 mL) and 5-{[(tert-butoxy)carbonyl]amino}pentanoic acid (181 mg, 0.83 mmol), HOBt (113 mg, 0.83 mmol) and EDC (160 mg, 0.83 mmol) were added. The reaction mixture was stirred for 3 d and concentrated in vacuo. The residue was dissolved in 1 M aq Na₂CO₃ (50 mL) and extracted with DCM (3×50 mL). The combined organic fractions were dried (MgSO₄) and concentrated in vacuo. The residue was purified by column chromatography and dissolved in DCM (10 mL) and TFA (2 mL) and stirred for 2 h. The reaction mixture was concentrated in vacuo and the residue was dissolved in 1 M aq Na₂CO₃ (50 mL) and extracted with DCM (3×50 mL). The combined organic fractions were dried (MgSO₄) and concentrated in vacuo. The residue was purified by column chromatography to give the title compound as a colourless gum (43.0 mg, 16%). HRMS (ESI+) calcd for C23H27ClN4O, 411.1946. found 411.1947. HPLC: Rf 3.84 min, 99% purity.

Example 5

N-(2-Aminoethyl)-4-[1-(4-chlorophenyl)-1H-pyrrolo[2,3-c]pyridin-3-yl]piperidine-1-carboxamide

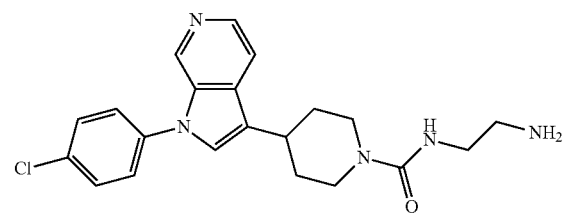 [SMILES: NCCNC(=O)N1CCC(c2cn(-c3ccc(Cl)cc3)c3cnccc23)CC1]

CDI (125 mg, 0.77 mmol) was dissolved in DCM (10 mL) and a solution of tert-butyl N-(2-aminoethyl)carbamate (123 mg, 0.77 mmol) and DIPEA (167 µL, 0.96 mmol) in DCM (1 mL) was added. The reaction mixture was stirred for 18 h, a solution of Intermediate 4 (200 mg, 0.64 mmol) and DIPEA (167 µL, 0.96 mmol) in DCM (1 mL) was added, and the reaction mixture was stirred for 24 h. The reaction mixture was diluted with EtOAc (50 mL), washed with 10% aq citric acid (50 mL) and 1 M Na₂CO₃ (50 mL), dried (MgSO₄) and concentrated in vacuo. The residue was dissolved in DCM (5 mL) and TFA (1 mL) and stirred for 1 h. The reaction mixture was concentrated in vacuo and the residue was purified by reverse phase HPLC to give the title compound as a colourless gum (36.0 mg, 14%). HRMS (ESI+) calcd for C21H24ClN5O, 398.1742. found 398.1745. HPLC: Rf 3.71 min, 99% purity.

Example 6

N-(3-Aminopropyl)-4-[1-(4-chlorophenyl)-1H-pyrrolo[2,3-c]pyridin-3-yl]piperidine-1-carboxamide

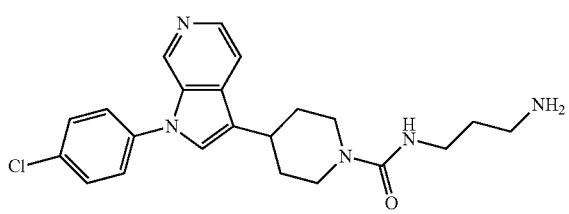 [SMILES: NCCCNC(=O)N1CCC(c2cn(-c3ccc(Cl)cc3)c3cnccc23)CC1]

Example 6 (178 mg, 8%) was prepared similarly to Example 5, using tert-butyl N-(3-aminopropyl)carbamate instead of tert-butyl N-(2-aminoethyl)carbamate. HRMS (ESI+) calcd for C22H26ClN5O, 412.1899. found 412.1902. HPLC: Rf 3.82 min, 100% purity.

Example 7

4-[1-(4-Chlorophenyl)-1H-pyrrolo[2,3-c]pyridin-3-yl]-N-[3-(dimethylamino) propyl]piperidine-1-carboxamide

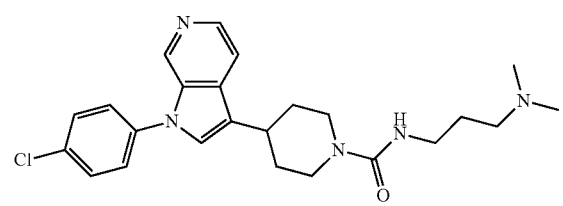 [SMILES: CN(C)CCCNC(=O)N1CCC(c2cn(-c3ccc(Cl)cc3)c3cnccc23)CC1]

Example 7 (99.0 mg, 23%) was prepared similarly to Example 5, using (3-aminopropyl)dimethylamine instead of tert-butyl N-(2-aminoethyl)carbamate (and no deprotection step). HRMS (ESI+) calcd for C24H30ClN5O, 440.2212. found 440.2213. HPLC: Rf 3.99 min, 99.7% purity.

Example 8

1-({4-[1-(4-Chlorophenyl)-1H-pyrrolo[2,3-c]pyridin-3-yl]piperidin-1-yl}carbonyl)piperazine

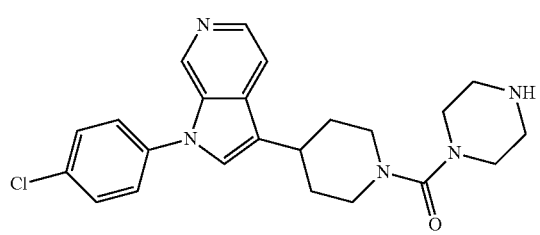 [SMILES: O=C(N1CCNCC1)N1CCC(c2cn(-c3ccc(Cl)cc3)c3cnccc23)CC1]

Triphosgene (111 mg, 0.37 mmol) was dissolved in DCM (10 mL) and a solution of tert-butyl 1-piperazinecarboxylate (210 mg, 1.13 mmol) and DIPEA (215 μL, 1.24 mmol) in DCM (2 mL) was added. The reaction mixture was stirred for 18 h and a solution of Intermediate 4 (351 mg, 1.13 mmol), DIPEA (215 μL, 1.24 mmol) and DMAP (13.7 mg, 0.11 mmol) in DCM (2 mL) was added. The reaction mixture was stirred for 24 h, diluted with 1 M aq $Na_2CO_3$ (50 mL) and extracted with DCM (3×50 mL). The combined organic fractions were dried ($MgSO_4$) and concentrated in vacuo. The residue was purified by column chromatography, dissolved in DCM (10 mL) and TFA (2.5 mL) and stirred for 1 h. The solvents were removed in vacuo and the residue was dissolved in 1 M aq $Na_2CO_3$ (50 mL) and extracted with DCM (3×50 mL). The combined organic fractions were dried ($MgSO_4$) and concentrated in vacuo.

The residue was purified by reverse phase HPLC to give the title compound as a white solid (54.0 mg, 11%). HRMS (ESI+) calcd for C23H26ClN5O, 424.1899. found 424.19. HPLC: Rf 3.93 min, 100% purity.

Example 9

4-({4-[1-(4-Chlorophenyl)-1H-pyrrolo[2,3-c]pyridin-3-yl]piperidin-1-yl}carbonyl)morpholine

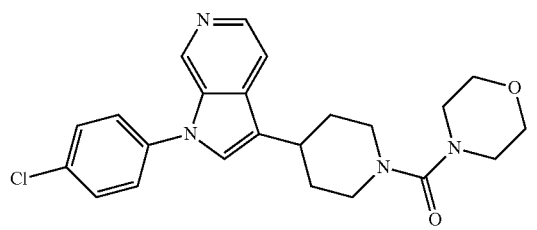 [SMILES: O=C(N1CCOCC1)N1CCC(c2cn(-c3ccc(Cl)cc3)c3cnccc23)CC1]

Intermediate 4 (300 mg, 0.96 mmol), DIPEA (184 μL, 1.06 mmol) and DMAP (11.7 mg, 0.10 mmol) were dissolved in DCM (10 mL) and 4-morpholinecarbonyl chloride (158 mg, 1.06 mmol) was added. The reaction mixture was stirred for 18 h, diluted with 1 M aq $Na_2CO_3$ (50 mL) and extracted with DCM (3×50 mL). The combined organic fractions were dried ($MgSO_4$) and concentrated in vacuo. The residue was purified by reverse phase HPLC to give the title compound as a white solid (252 mg, 62%). HRMS (ESI+) calcd for C23H25ClN4O2 425.1739. found 425.1742. HPLC: Rf 4.79 min, 96% purity.

Example 10

1-({4-[1-(4-Chlorophenyl)-1H-pyrrolo[2,3-c]pyridin-3-yl]piperidin-1-yl}carbonyl)-1,4-diazepane

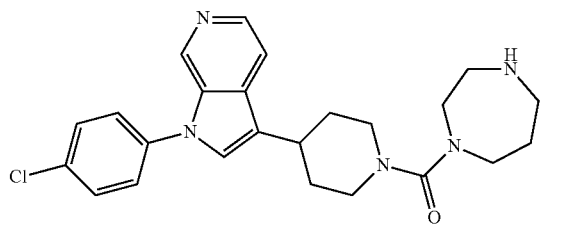 [SMILES: O=C(N1CCCNCC1)N1CCC(c2cn(-c3ccc(Cl)cc3)c3cnccc23)CC1]

Example 10 (70.0 mg, 20%) was prepared similarly to Example 8, using tert-butyl 1,4-diazepane-1-carboxylate instead of tert-butyl 1-piperazinecarboxylate. HRMS (ESI+) calcd for C24H28ClN5O, 438.2055. found 438.2056. HPLC: Rf 3.94 min, 100% purity.

Example 11

Ethyl 1-[1-(4-chlorophenyl)-1H-pyrazolo[3,4-c]pyridin-3-yl]piperidine-4-carboxylate

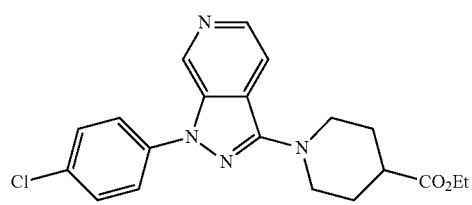 [SMILES: CCOC(=O)C1CCN(c2nn(-c3ccc(Cl)cc3)c3cnccc23)CC1]

Intermediate 13 (3.49 g, 12.7 mmol), 4-chlorophenylboronic acid (3.98 g, 25.5 mmol), $Cu(OAc)_2$ (4.63 g, 25.5 mmol) and pyridine (5.13 mL, 63.7 mmol) were suspended in DCE (88 mL) and stirred overnight. The reaction mixture was purified by column chromatography to give the title compound as an off-white solid (619 mg, 13%). HRMS (ESI+) calcd for C20H21ClN4O2 385.1426. found 385.143. HPLC: Rf 6.13 min, 98.9% purity.

Example 12

Ethyl 1-[1-(4-methylphenyl)-1H-pyrazolo[3,4-c]pyridin-3-yl]piperidine-4-carboxylate

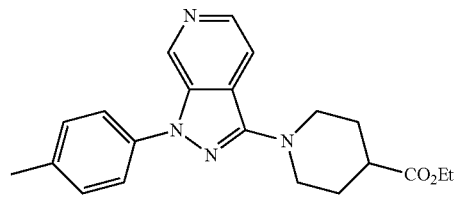 [SMILES: CCOC(=O)C1CCN(c2nn(-c3ccc(C)cc3)c3cnccc23)CC1]

Example 12 was prepared similarly to Example 11, using 4-methylbenzeneboronic acid instead of 4-chlorophenylboronic acid, to give the title compound as a white solid (74.0 mg, 56%). HRMS (ESI+) calcd for C21H24N4O2 365.1972. found 365.1975. HPLC: Rf 5.87 min, 99.1% purity.

Example 13

1-[1-(4-Chlorophenyl)-1H-pyrazolo[3,4-c]pyridin-3-yl]piperidine-4-carboxylic acid hydrochloride

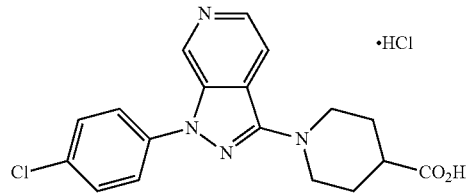 [SMILES: O=C(O)C1CCN(c2nn(-c3ccc(Cl)cc3)c3cnccc23)CC1 ; Cl]

Example 11 (834 mg, 2.17 mmol) was dissolved in 1:1 THF/water (16 mL), LiOH.H$_2$O (200 mg, 4.77 mmol) was added and the reaction mixture was stirred for 3 h. The THF was removed in vacuo and the reaction mixture was acidified to pH 1 with 1 M aq HCl (5 mL). The precipitate was collected by filtration and washed with water to give the title compound as an orange solid (450 mg, 53%). HRMS (ESI+) calcd for C18H17ClN4O2 357.1113. found 357.1112. HPLC: Rf 4.92 min, 99.6% purity.

Example 14

N-(2-Aminoethyl)-1-[1-(4-chlorophenyl)-1H-pyrazolo[3,4-c]pyridin-3-yl]piperidine-4-carboxamide dihydrochloride

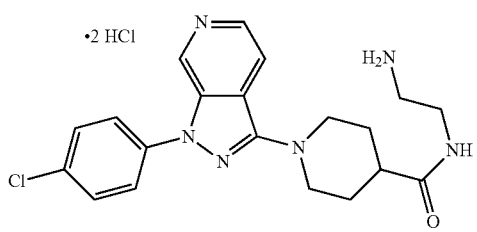 [SMILES: NCCNC(=O)C1CCN(c2nn(-c3ccc(Cl)cc3)c3cnccc23)CC1 ; "·2 HCl"]

Example 13 (200 mg, 0.51 mmol) was dissolved in DMF (2 mL), HBTU (231 mg, 0.61 mmol was added and the reaction mixture was stirred for 30 min. tert-Butyl N-(2-aminoethyl)carbamate (97.8 mg, 0.61 mmol) and DIPEA (266 mL, 1.53 mmol) were added and the reaction mixture was stirred overnight. The reaction mixture was concentrated in vacuo and triturated twice from EtOAc (25 mL) and MeOH (10 mL). The residue was dissolved in 1.25 M HCl in EtOH (5 mL), stirred for 20 h and concentrated in vacuo to yield the title compound as an orange solid (50.1 mg, 95%). HRMS (ESI+) calcd for C20H23ClN6O, 399.1695. found 399.1694. HPLC: Rf 3.96 min, 99.8% purity.

Example 15

4-({1-[1-(4-Chlorophenyl)-1H-pyrazolo[3,4-c]pyridin-3-yl]piperidin-4-yl}carbonyl) morpholine

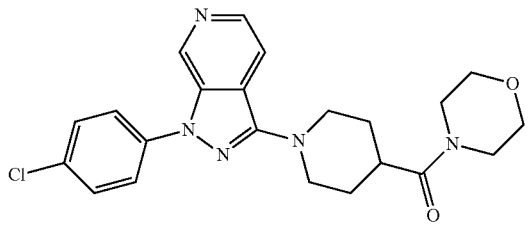 [SMILES: O=C(C1CCN(c2nn(-c3ccc(Cl)cc3)c3cnccc23)CC1)N1CCOCC1]

Example 15 was prepared similarly to Example 14, using morpholine instead of tert-Butyl N-(2-aminoethyl)carbamate (and no deprotection step) to give the title compound as a light yellow solid (78.7 mg, 36%). HRMS (ESI+) calcd for C22H24ClN5O2 426.1691. found 426.1691. HPLC: Rf 4.96 min, 100% purity.

Example 16

1-({1-[1-(4-Chlorophenyl)-1H-pyrazolo[3,4-c]pyridin-3-yl]piperidin-4-yl}carbonyl)piperazine dihydrochloride

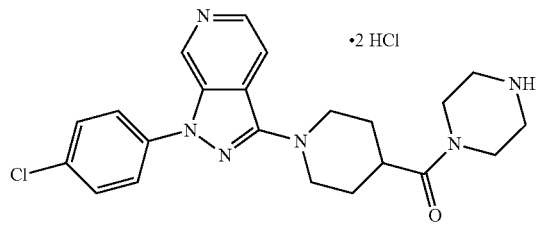 [SMILES: O=C(C1CCN(c2nn(-c3ccc(Cl)cc3)c3cnccc23)CC1)N1CCNCC1]

Example 16 was prepared similarly to Example 14, using tert-Butyl 1-piperazinecarboxylate instead of tert-Butyl N-(2-aminoethyl)carbamate to give the title compound as an orange solid (122 mg, 96%). HRMS (ESI+) calcd for C22H25ClN6O, 425.1851. found 425.1846. HPLC: Rf 3.98 min, 98.8% purity.

Example 17

{4-[1-(4-Methylphenyl)-1H-pyrazolo[3,4-c]pyridin-3-yl]morpholin-3-yl}methanol

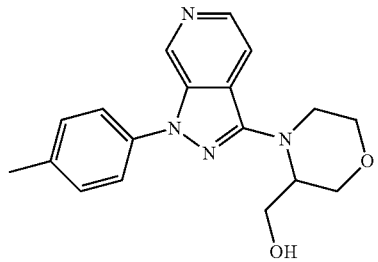 [SMILES: Cc1ccc(-n2nc(N3CCOCC3CO)c3ccncc32)cc1]

Intermediate 21 (50.0 mg, 0.14 mmol) was dissolved in MeOH (1 mL), K$_2$CO$_3$ (75.4 mg, 0.55 mmol) was added and the reaction mixture was stirred for 30 min. The reaction mixture was concentrated in vacuo and the residue partitioned between DCM (10 mL) and water (5 mL). The aq fraction was extracted with DCM (3×10 mL) and the combined organic fractions were dried (MgSO$_4$) and concentrated in vacuo to give the title compound as a yellow gum (40.0 mg, 90%). LCMS (ES$^+$): 325.1 [MH]$^+$. HPLC: Rf 4.36 min, 94.9% purity.

Example 18

{4-[1-(4-Methylphenyl)-1H-pyrazolo[3,4-c]pyridin-3-yl]morpholin-2-yl}methanol

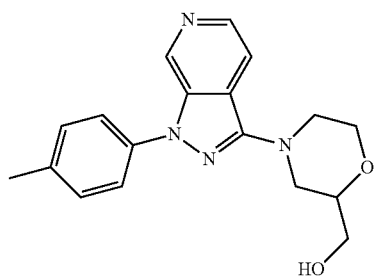

Example 18 was prepared similarly to Example 17, using Intermediate 22 instead of Intermediate 21, to give the title compound as an orange gum (3.74 mg, 36%). HRMS (ESI+) calcd for C18H20N4O2 325.1659. found 325.1663. HPLC: Rf 4.29 min, 98.8% purity.

Example 19

[(3R)-4-[1-(4-Chlorophenyl)-1H-pyrazolo[3,4-c]pyridin-3-yl]morpholin-3-yl]methanol

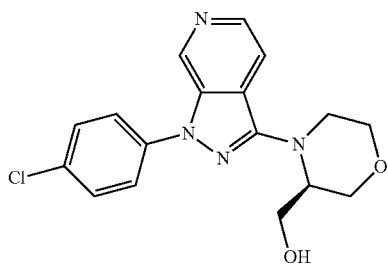 [SMILES: OC[C@@H]1COCCN1c1nn(-c2ccc(Cl)cc2)c2cnccc12]

Example 19 was prepared similarly to Example 11, using Intermediate 15 instead of Intermediate 13, to give the title compound as a dark yellow gum (11.6 mg). HRMS (ESI+) calcd for C17H17ClN4O2 345.1113. found 345.1117. HPLC: Rf 4.58 min, 100% purity.

Example 20

Methyl 4-[1-(4-chlorophenyl)-1H-pyrazolo[3,4-c]pyridin-3-yl]morpholine-3-carboxylate

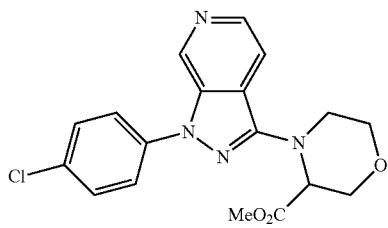 [SMILES: COC(=O)C1COCCN1c1nn(-c2ccc(Cl)cc2)c2cnccc12]

Example 20 was prepared similarly to Example 11, using Intermediate 18 instead of Intermediate 13, to give the title compound as a dark yellow solid (552 mg, 20%). HRMS (ESI+) calcd for C18H17ClN4O3 373.1062. found 373.1065. HPLC: Rf 5.23 min, 98.0% purity.

Example 21

N-(2-Aminoethyl)-4-[1-(4-chlorophenyl)-1H-pyrazolo[3,4-c]pyridin-3-yl]morpholine-3-carboxamide

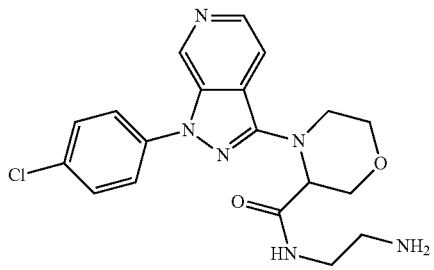 [SMILES: NCCNC(=O)C1COCCN1c1nn(-c2ccc(Cl)cc2)c2cnccc12]

Intermediate 25 (70.0 mg, 0.18 mmol) was dissolved in DMF (1.1 mL), cooled to 0° C. and HBTU (67.2 mg, 0.18 mmol), tert-butyl N-(2-aminoethyl)carbamate (34.1 mg, 0.21 mmol) and DIPEA (30.9 µL, 0.18 mmol) were added. The reaction mixture was stirred at 0° C. for 2.5 h and purified by column chromatography. The residue dissolved in 1.25 M HCl in EtOH (1.00 mL) and stirred for 2 h. The reaction mixture was concentrated in vacuo and purified by column chromatography to give the title compound as a pale yellow solid (3.09 mg, 4%). HRMS (ESI+) calcd for C19H21ClN6O2 401.1487. found 401.149. HPLC: Rf 3.83 min, 100% purity.

Example 22

2-{4-[1-(4-Chlorophenyl)-1H-pyrazolo[3,4-c]pyridin-3-yl]morpholin-3-yl}ethan-1-ol

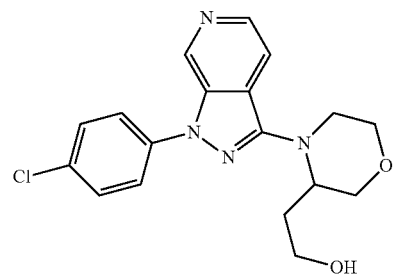 [SMILES: OCCC1COCCN1c1nn(-c2ccc(Cl)cc2)c2cnccc12]

Intermediate 24 (50.0 mg, 0.13 mmol) was dissolved in DCM (1 mL), cooled to 0° C. and DIBALH (0.47 mL, 1.0 M in heptane, 0.47 mmol) was added drop-wise. The reaction mixture was stirred for 48 h, cooled to 0° C. and quenched with sat aq NaHCO3 (1 mL). The reaction mixture was extracted with DCM (5×20 mL) and the combined organic fractions were dried (MgSO4) and concentrated in vacuo. The residue was purified by reverse phase chromatography to give the title compound as a pale yellow solid (13.9 mg, 30%). HRMS (ESI+) calcd for C18H19ClN4O2 359.1269. found 359.1274. HPLC: Rf 4.72 min, 99.5% purity.

Example 23

Methyl 1-[1-(4-chlorophenyl)-1H-pyrazolo[3,4-c]pyridin-3-yl]piperidine-2-carboxylate

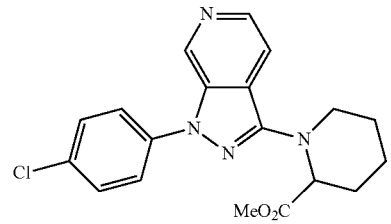 [SMILES: COC(=O)C1CCCCN1c1nn(-c2ccc(Cl)cc2)c2cnccc12]

Example 23 was prepared similarly to Example 11, using Intermediate 20 instead of Intermediate 13, to give the title compound as a dark yellow solid (260 mg, 28%). HRMS (ESI+) calcd for C19H19ClN4O2 371.1269. found 371.1273. HPLC: Rf 5.91 min, 99.3% purity.

Example 24

N-(2-Aminoethyl)-1-[1-(4-chlorophenyl)-1H-pyrazolo[3,4-c]pyridin-3-yl]piperidine-2-carboxamide dihydrochloride

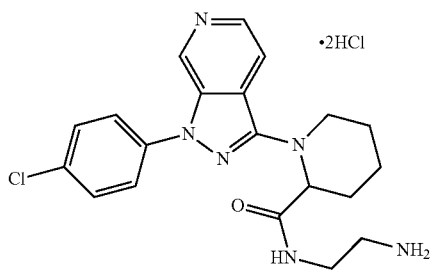 [SMILES: NCCNC(=O)C1CCCCN1c1nn(-c2ccc(Cl)cc2)c2cnccc12]

Example 24 was prepared similarly to Example 21, using Intermediate 26 instead of Intermediate 25, to give the title compound as an orange solid (22.5 mg, 28%). LCMS (ES+): 399.0 [MH]$^+$. HPLC: Rf 4.10 min, 98.5% purity.

Example 25

1-({1-[1-(4-Chlorophenyl)-1H-pyrazolo[3,4-c]pyridin-3-yl]piperidin-2-yl}carbonyl) piperazine

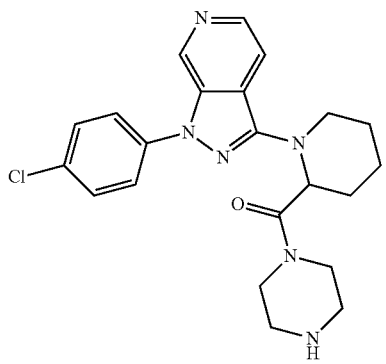 [SMILES: O=C(C1CCCCN1c1nn(-c2ccc(Cl)cc2)c2cnccc12)N1CCNCC1]

Example 25 was prepared similarly to Example 24, using tert-butyl 1-piperazinecarboxylate instead of tert-butyl N-(2-aminoethyl)carbamate, to give the title compound as a yellow solid (10.3 mg, 14%). LCMS (ES+): 424.9 [MH]$^+$. HPLC: Rf 3.91 min, 99.5% purity.

Example 26

4-[1-(4-Methylphenyl)-1H-pyrrolo[2,3-c]pyridin-3-yl]morpholine

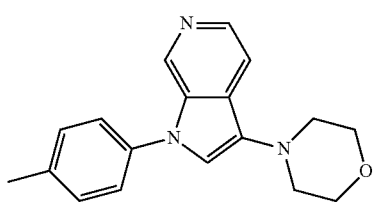 [SMILES: Cc1ccc(-n2cc(N3CCOCC3)c3ccncc32)cc1]

Intermediate 31 (81.0 mg, 0.40 mmol), 4-iodotoluene (104 mg, 0.48 mmol), N,N'-dimethylethylenediamine (8.58 μL, 0.08 mmol) and K$_3$PO$_4$ (178 mg, 0.84 mmol) were suspended in DMF (1 mL) and CuI (7.60 mg, 0.04 mmol) was added. The reaction mixture was heated at 170° C. in a microwave reactor for 1 h and concentrated in vacuo. The residue was diluted with MeOH (15 mL), filtered, concentrated in vacuo and purified by reverse phase HPLC and normal phase column chromatography to give the title compound as a dark yellow gum (2.00 mg, 2%). HRMS (ESI+) calcd for C18H19N3O, 294.1601. found 294.1604. HPLC: Rf 4.43 min, 100% purity.

Example 27

1-(4-Chlorophenyl)-3-(piperidin-4-yl)-1H-pyrrolo[2,3-c]pyridin-4-ol

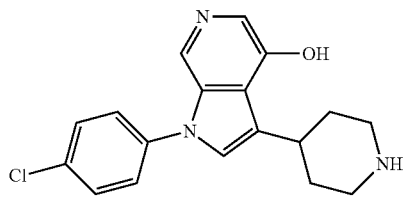 [SMILES: Oc1cncc2c1c(C1CCNCC1)cn2-c1ccc(Cl)cc1]

Intermediate 36 (130 mg, 0.29 mmol) was dissolved in DCM (10 mL), BBr$_3$ (84 μL, 0.88 mmol) was added and the reaction mixture was stirred for 3 h, quenched with 1 M aq NaOH (1 mL) and stirred for 1 h. The reaction mixture was diluted with sat aq NaHCO$_3$ (25 mL) and extracted with DCM (3×25 mL). The aq fraction was acidified to pH 9 with AcOH and extracted with EtOAc (2×25 mL). The combined organic fractions were dried (MgSO$_4$) and concentrated in vacuo. The residue was purified by reverse phase HPLC to give the title compound as a colourless gum (8.40 mg, 9%). HRMS (ESI+) calcd for C18H18ClN3O, 328.1211. found 328.1216. HPLC: Rf 3.70 min, 89% purity.

Example 28

N-Butyl-1-(4-chlorophenyl)-N-methyl-1H-pyrazolo[3,4-c]pyridin-3-amine

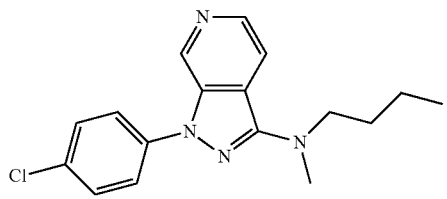 [SMILES: CCCCN(C)c1nn(-c2ccc(Cl)cc2)c2cnccc12]

Example 28 was prepared similarly to Example 26, using Intermediate 17 instead of Intermediate 31, and 1-chloro-4-iodobenzene instead of 4-iodotoluene, to give the title compound as a yellow gum (212 mg, 22%). HRMS (ESI+) calcd for C17H19ClN4 315.1371. found 315.1375. HPLC: Rf 6.54 min, 100% purity.

Example 29

1-[4-(Fluoromethyl)phenyl]-3-(oxan-4-yl)-1H-pyrazolo[3,4-c]pyridine

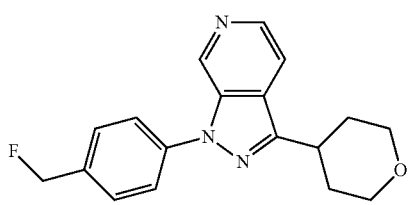 [SMILES: FCc1ccc(-n2nc(C3CCOCC3)c3ccncc32)cc1]

Example 29 was prepared similarly to Example 26, using Intermediate 39 instead of Intermediate 31, and 1-bromo-4-fluoromethylbenzene instead of 4-iodotoluene, to give the title compound as a yellow gum (36.6 mg, 7%). HRMS (ESI+) calcd for C18H18FN3O, 312.1507, found 312.151. HPLC: Rf 4.84 min, 99.2% purity.

Example 30

3-({4-[1-(4-Chlorophenyl)-1H-pyrazolo[3,4-c]pyridin-3-yl]piperidin-1-yl}methyl)pyridine

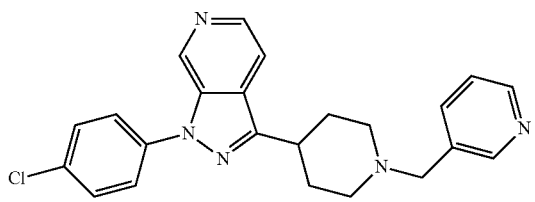 [SMILES: Clc1ccc(-n2nc(C3CCN(Cc4cccnc4)CC3)c3ccncc32)cc1]

Intermediate 44 (232 mg, 0.74 mmol) was dissolved in DCM (25 mL) and 3-pyridinecarboxaldehyde (167 µl, 1.78 mmol), AcOH (44.6 µL, 0.78 mmol) and NaBH(OAc)$_3$ (472 mg, 2.23 mmol) were added. The reaction was stirred for 18 h, diluted with DCM (50 mL) and quenched with water (20 mL). The organic fraction was washed with sat aq Na$_2$CO$_3$ (20 mL), dried (MgSO$_4$) and concentrated in vacuo. The residue was purified by reverse phase HPLC to give the title compound as a brown gum (63.7 mg, 21%). HRMS (ESI+) calcd for C23H22ClN5 404.1636. found 404.1639. HPLC: Rf 4.63 min, 98.3% purity.

Biological Tests

Biological Assays of the SSAO Enzyme Inhibitors

All primary assays were performed at RT. with purified recombinantly expressed human SSAO. Enzyme was prepared essentially as described in Ohman et al. (Protein Expression and Purification 46 (2006) 321 331). In addition, secondary- and selectivity assays were performed using SSAO prepared from various tissues or purified rat recombinant SSAO. The enzyme activity was assayed with benzylamine as substrate by measuring either benzaldehyde production, using $^{14}$C-labeled substrate, or by utilizing the production of hydrogen peroxide in a horseradish peroxidase (HRP) coupled reaction. Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer yielded a final DMSO concentration ≤2%.

Hydrogen Peroxide Detection:

In a horseradish peroxidase (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidase Assay kit, Invitrogen A22188). Enzyme and compounds in 50 mM sodium phosphate, pH 7.4 were set to pre-incubate in flat-bottomed microtiter plates for approximately 15 minutes before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 hours, exciting at 544 nm and reading the emission at 590 nm. For the human SSAO assay final concentrations of the reagents in the assay wells were: SSAO enzyme 1 µg/ml, benzylamine 100 µM, Amplex reagent 20 µM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and IC$_{50}$ values were calculated using the GraphPad Prism 4 or XLfit 4 programs.

Aldehyde Detection:

SSAO activity was assayed using 14C-labeled benzylamine and analysed by measuring radioactive benzaldehyde. In a white 96-well optiplate (Packard), 20 µL of diluted test compound was pre-incubated at RT. with 20 µL SSAO enzyme for approximately 15 minutes with continuous agitation. All dilutions were made with PBS. The reaction was initiated by adding 20 µL of the benzylamine substrate solution containing [7-14C] Benzylamine hydrochloride (CFA589, GE Healthcare). The plate was incubated for 1 hour as above after which the reaction was stopped by acidification (10 µL 1 M HCl). Then 90 µL Micro Scint-E solution (PerkinElmer) was added to each well and the plate was continuously mixed for 15 minutes. Phase separation occurred instantly and activity was read in a Topcount scintillation counter (Perkin-Elmer). In the final reaction well, the human recombinant SSAO concentration was 10 µg/ml. In order to optimize sensitivity, the substrate concentration was decreased as compared to the HRP coupled assay in order to get a higher fraction of radioactive product. In the human SSAO assay, benzylamine concentration was 40 µM (0.2 µCi/mL). Data was analysed as above.

All of the exemplified compounds of the invention had an IC$_{50}$ value of 1-2500 nM at SSAO (See Table 4).

TABLE 4

| SSAO inhibitory activity | |
|---|---|
| Compound | IC$_{50}$ (nM) |
| 1 | A |
| 2 | A |
| 3 | A |
| 4 | A |
| 5 | A |
| 6 | A |

TABLE 4-continued

SSAO inhibitory activity

| Compound | IC$_{50}$ (nM) |
|---|---|
| 7 | A |
| 8 | A |
| 9 | B |
| 10 | A |
| 11 | C |
| 12 | B |
| 13 | B |
| 14 | B |
| 15 | C |
| 16 | B |
| 17 | A |
| 18 | A |
| 19 | A |
| 20 | B |
| 21 | A |
| 22 | A |
| 23 | C |
| 24 | A |
| 25 | A |
| 26 | B |
| 27 | A |
| 28 | C |
| 29 | B |
| 30 | B |

(A: <100 nM, B: 100-500 nM, C: 500-2500 nM)

The invention claimed is:

1. A compound selected from the group consisting of:
2-{4-[1-(4-chlorophenyl)-1H-pyrrolo[2,3-c]pyridin-3-yl]piperidin-1-yl}ethan-1-amine;
3-aminopropyl 4-[1-(4-chlorophenyl)-1H-pyrrolo[2,3-c]pyridin-3-yl]piperidine-1-carboxylate;
1-{4-[1-(4-chlorophenyl)-1H-pyrrolo[2,3-c]pyridin-3-yl]piperidin-1-yl}-4-(dimethylamino)butan-1-one;
5-amino-1-{4-[1-(4-chlorophenyl)-1H-pyrrolo[2,3-c]pyridin-3-yl]piperidin-1-yl}pentan-1-one;
N-(2-aminoethyl)-4-[1-(4-chlorophenyl)-1H-pyrrolo[2,3-c]pyridin-3-yl]piperidine-1-carboxamide;
N-(3-aminopropyl)-4-[1-(4-chlorophenyl)-1H-pyrrolo[2,3-c]pyridin-3-yl]piperidine-1-carboxamide;
4-[1-(4-chlorophenyl)-1H-pyrrolo[2,3-c]pyridin-3-yl]-N-[3-(dimethylamino)propyl]piperidine-1-carboxamide;
1-({4-[1-(4-chlorophenyl)-1H-pyrrolo[2,3-c]pyridin-3-yl]piperidin-1-yl}carbonyl)piperazine;
4-({4-[1-(4-chlorophenyl)-1H-pyrrolo[2,3-c]pyridin-3-yl]piperidin-1-yl}carbonyl)morpholine;
1-({4-[1-(4-chlorophenyl)-1H-pyrrolo[2,3-c]pyridin-3-yl]piperidin-1-yl}carbonyl)-1,4-diazepane;
ethyl 1-[1-(4-chlorophenyl)-1H-pyrazolo[3,4-c]pyridin-3-yl]piperidine-4-carboxylate;
ethyl 1-[1-(4-methylphenyl)-1H-pyrazolo[3,4-c]pyridin-3-yl]piperidine-4-carboxylate;
1-[1-(4-chlorophenyl)-1H-pyrazolo[3,4-c]pyridin-3-yl]piperidine-4-carboxylic acid;
N-(2-aminoethyl)-1-[1-(4-chlorophenyl)-1H-pyrazolo[3,4-c]pyridin-3-yl]piperidine-4-carboxamide;
4-({1-[1-(4-chlorophenyl)-1H-pyrazolo[3,4-c]pyridin-3-yl]piperidin-4-yl}carbonyl)morpholine;
1-({1-[1-(4-chlorophenyl)-1H-pyrazolo[3,4-c]pyridin-3-yl]piperidin-4-yl}carbonyl)piperazine;
{4-[1-(4-methylphenyl)-1H-pyrazolo[3,4-c]pyridin-3-yl]morpholin-3-yl}methanol;
{4-[1-(4-methylphenyl)-1H-pyrazolo[3,4-c]pyridin-3-yl]morpholin-2-yl}methanol;
[(3R)-4-[1-(4-chlorophenyl)-1H-pyrazolo[3,4-c]pyridin-3-yl]morpholin-3-yl]methanol;
methyl 4-[1-(4-chlorophenyl)-1H-pyrazolo[3,4-c]pyridin-3-yl]morpholine-3-carboxylate;
N-(2-aminoethyl)-4-[1-(4-chlorophenyl)-1H-pyrazolo[3,4-c]pyridin-3-yl]morpholine-3-carboxamide;
2-{4-[1-(4-chlorophenyl)-1H-pyrazolo[3,4-c]pyridin-3-yl]morpholin-3-yl}ethan-1-ol;
methyl 1-[1-(4-chlorophenyl)-1H-pyrazolo[3,4-c]pyridin-3-yl]piperidine-2-carboxylate;
N-(2-aminoethyl)-1-[1-(4-chlorophenyl)-1H-pyrazolo[3,4-c]pyridin-3-yl]piperidine-2-carboxamide;
1-({1-[1-(4-chlorophenyl)-1H-pyrazolo[3,4-c]pyridin-3-yl]piperidin-2-yl}carbonyl)piperazine;
4-[1-(4-methylphenyl)-1H-pyrrolo[2,3-c]pyridin-3-yl]morpholine;
1-(4-chlorophenyl)-3-(piperidin-4-yl)-1H-pyrrolo[2,3-c]pyridin-4-ol;
N-butyl-1-(4-chlorophenyl)-N-methyl-1H-pyrazolo[3,4-c]pyridin-3-amine;
1-[4-(fluoromethyl)phenyl]-3-(oxan-4-yl)-1H-pyrazolo[3,4-c]pyridine;
3-({4-[1-(4-chlorophenyl)-1H-pyrazolo[3,4-c]pyridin-3-yl]piperidin-1-yl}methyl)pyridine;
and pharmaceutically acceptable salts thereof.

2. A pharmaceutical composition comprising a compound as claimed in claim 1, together with one or more pharmaceutically acceptable carriers and/or excipients.

3. The compound of claim 1, wherein the compound is selected from the group consisting of:
2-{4-[1-(4-chlorophenyl)-1H-pyrrolo[2,3-c]pyridin-3-yl]piperidin-1-yl}ethan-1-amine;
3-aminopropyl 4-[1-(4-chlorophenyl)-1H-pyrrolo[2,3-c]pyridin-3-yl]piperidine-1-carboxylate;
1-{4-[1-(4-chlorophenyl)-1H-pyrrolo[2,3-c]pyridin-3-yl]piperidin-1-yl}-4-(dimethylamino)butan-1-one;
5-amino-1-{4-[1-(4-chlorophenyl)-1H-pyrrolo[2,3-c]pyridin-3-yl]piperidin-1-yl}pentan-1-one;
N-(2-aminoethyl)-4-[1-(4-chlorophenyl)-1H-pyrrolo[2,3-c]pyridin-3-yl]piperidine-1-carboxamide;
N-(3-aminopropyl)-4-[1-(4-chlorophenyl)-1H-pyrrolo[2,3-c]pyridin-3-yl]piperidine-1-carboxamide;
4-[1-(4-chlorophenyl)-1H-pyrrolo[2,3-c]pyridin-3-yl]-N-[3-(dimethylamino)propyl]piperidine-1-carboxamide;
1-({4-[1-(4-chlorophenyl)-1H-pyrrolo[2,3-c]pyridin-3-yl]piperidin-1-yl}carbonyl)piperazine;
4-({4-[1-(4-chlorophenyl)-1H-pyrrolo[2,3-c]pyridin-3-yl]piperidin-1-yl}carbonyl)morpholine;
1-({4-[1-(4-chlorophenyl)-1H-pyrrolo[2,3-c]pyridin-3-yl]piperidin-1-yl}carbonyl)-1,4-diazepane;
4-[1-(4-methylphenyl)-1H-pyrrolo[2,3-c]pyridin-3-yl]morpholine;
1-(4-chlorophenyl)-3-(piperidin-4-yl)-1H-pyrrolo[2,3-c]pyridin-4-ol;
and pharmaceutically acceptable salts thereof.

4. The compound of claim 1, wherein the compound is selected from the group consisting of:
ethyl 1-[1-(4-chlorophenyl)-1H-pyrazolo[3,4-c]pyridin-3-yl]piperidine-4-carboxylate;
ethyl 1-[1-(4-methylphenyl)-1H-pyrazolo[3,4-c]pyridin-3-yl]piperidine-4-carboxylate;
1-[1-(4-chlorophenyl)-1H-pyrazolo[3,4-c]pyridin-3-yl]piperidine-4-carboxylic acid;
N-(2-aminoethyl)-1-[1-(4-chlorophenyl)-1H-pyrazolo[3,4-c]pyridin-3-yl]piperidine-4-carboxamide;
4-({1-[1-(4-chlorophenyl)-1H-pyrazolo[3,4-c]pyridin-3-yl]piperidin-4-yl}carbonyl)morpholine;
1-({1-[1-(4-chlorophenyl)-1H-pyrazolo[3,4-c]pyridin-3-yl]piperidin-4-yl}carbonyl)piperazine;

{4-[1-(4-methylphenyl)-1H-pyrazolo[3,4-c]pyridin-3-yl]morpholin-3-yl}methanol;

{4-[1-(4-methylphenyl)-1H-pyrazolo[3,4-c]pyridin-3-yl]morpholin-2-yl}methanol;

[(3R)-4-[1-(4-chlorophenyl)-1H-pyrazolo[3,4-c]pyridin-3-yl]morpholin-3-yl]methanol;

methyl 4-[1-(4-chlorophenyl)-1H-pyrazolo[3,4-c]pyridin-3-yl]morpholine-3-carboxylate;

N-(2-aminoethyl)-4-[1-(4-chlorophenyl)-1H-pyrazolo[3,4-c]pyridin-3-yl]morpholine-3-carboxamide;

2-{4-[1-(4-chlorophenyl)-1H-pyrazolo[3,4-c]pyridin-3-yl]morpholin-3-yl}ethan-1-ol;

methyl 1-[1-(4-chlorophenyl)-1H-pyrazolo[3,4-c]pyridin-3-yl]piperidine-2-carboxylate;

N-(2-aminoethyl)-1-[1-(4-chlorophenyl)-1H-pyrazolo[3,4-c]pyridin-3-yl]piperidine-2-carboxamide;

1-({1-[1-(4-chlorophenyl)-1H-pyrazolo[3,4-c]pyridin-3-yl]piperidin-2-yl}carbonyl)piperazine;

N-butyl-1-(4-chlorophenyl)-N-methyl-1H-pyrazolo[3,4-c]pyridin-3-amine;

1-[4-(fluoromethyl)phenyl]-3-(oxan-4-yl)-1H-pyrazolo[3,4-c]pyridine;

3-({4-[1-(4-chlorophenyl)-1H-pyrazolo[3,4-c]pyridin-3-yl]piperidin-1-yl}methyl)pyridine;

and pharmaceutically acceptable salts thereof.

5. The compound of claim 4, wherein the compound is selected from the group consisting of:

{4-[1-(4-methylphenyl)-1H-pyrazolo[3,4-c]pyridin-3-yl]morpholin-3-yl}methanol;

{4-[1-(4-methylphenyl)-1H-pyrazolo[3,4-c]pyridin-3-yl]morpholin-2-yl}methanol;

[(3R)-4-[1-(4-chlorophenyl)-1H-pyrazolo[3,4-c]pyridin-3-yl]morpholin-3-yl]methanol;

methyl 4-[1-(4-chlorophenyl)-1H-pyrazolo[3,4-c]pyridin-3-yl]morpholine-3-carboxylate;

N-(2-aminoethyl)-4-[1-(4-chlorophenyl)-1H-pyrazolo[3,4-c]pyridin-3-yl]morpholine-3-carboxamide;

2-{4-[1-(4-chlorophenyl)-1H-pyrazolo[3,4-c]pyridin-3-yl]morpholin-3-yl}ethan-1-ol;

and pharmaceutically acceptable salts thereof.

6. A method for the treatment of inflammation or an inflammatory disease, which comprises administering to a subject suffering such disease an effective amount of a compound as claimed in claim 1.

7. The method of treatment of claim 6, wherein the inflammatory disease is rheumatoid arthritis, chronic obstructive pulmonary disease or atopic dermatitis.

8. The method of treatment of claim 6, wherein the inflammation or inflammatory disease is arthritis, synovitis, vasculitis, inflammation of the bowel, a pulmonary inflammatory disease, a fibrotic disease, an inflammatory disease of the skin, systemic inflammatory response syndrome, or sepsis.

9. The method of treatment of claim 8, wherein the arthritis is rheumatoid arthritis, juvenile rheumatoid arthritis, osteoarthritis or psoriatic arthritis.

10. The method of treatment of claim 8, wherein the inflammation of the bowel is Crohn's disease, ulcerative colitis, inflammatory bowel disease, or irritable bowel syndrome.

11. The method of treatment of claim 8, wherein the pulmonary inflammatory disease is asthma, chronic obstructive pulmonary disease, or acute respiratory distress syndrome.

12. The method of treatment of claim 8, wherein the inflammatory disease of the skin is contact dermatitis, atopic dermatitis or psoriasis.

\* \* \* \* \*